US012663150B2

(12) United States Patent     (10) Patent No.:   US 12,663,150 B2

Funk et al.     (45) Date of Patent:   Jun. 23, 2026

(54) FRAGRANCE DISPENSER WITH DECORATIVE COVER ASSEMBLY

(71) Applicant: BeautyAvenues, LLC, Reynoldsburg, OH (US)

(72) Inventors: Tobias Funk, Columbus, OH (US); Vanessa Mull, Columbus, OH (US); Anya Schmidt, Columbus, OH (US)

(73) Assignee: BeautyAvenues, LLC, Reynoldsburg, OH (US)

( * ) Notice: Subject to any disclaimer, the term of this patent is extended or adjusted under 35 U.S.C. 154(b) by 0 days.

(21) Appl. No.: 19/265,006

(22) Filed: Jul. 10, 2025

(65) Prior Publication Data

US 2025/0334263 A1     Oct. 30, 2025

Related U.S. Application Data

(63) Continuation-in-part of application No. 18/106,762, filed on Feb. 7, 2023.

(51) Int. Cl.
*F21V 33/00*     (2006.01)
*A61L 9/03*     (2006.01)
*F21V 3/02*     (2006.01)

(52) U.S. Cl.
CPC .......... *F21V 33/0024* (2013.01); *A61L 9/037* (2013.01); *F21V 3/02* (2013.01); *A61L 2209/12* (2013.01); *A61L 2209/133* (2013.01)

(58) Field of Classification Search
CPC .................................................. A61L 2209/12
See application file for complete search history.

(56) References Cited

U.S. PATENT DOCUMENTS

| | | |
|---|---|---|
| 4,549,250 A | 10/1985 | Spector |
| 5,437,540 A | 8/1995 | Blocker |
| 6,236,807 B1 | 5/2001 | Ruffolo et al. |
| D493,876 S | 8/2004 | Wirthman et al. |
| D493,877 S | 8/2004 | Wirthman et al. |
| D495,046 S | 8/2004 | Wirthman et al. |
| D497,422 S | 10/2004 | Wirthman et al. |
| D501,545 S | 2/2005 | Wirthman et al. |
| D506,817 S | 6/2005 | Wirthman et al. |
| D507,636 S | 7/2005 | Baraky et al. |
| D522,119 S | 5/2006 | Baraky et al. |
| D544,087 S | 6/2007 | Baraky et al. |

(Continued)

OTHER PUBLICATIONS

Hyde & Eek Blinking Eye Cat LED Light Motion Projector Halloween Decor Yard New, item available on ebay.com, 2022, available at https://www.ebay.com/itm/276151920148?chn=ps &norover=1&mkevt=1&mkrid=711-117182-37290-0&mkcid=2 &mkscid=101&itemid=276151920148&targetid=2295557533150 &device=c&mktype=pla&googleloc=9014904&poi=&campaignid= 19851828444&mkgroupid=160536780385&rlsatarget=pla-2295557533150&abcld=9307249&merchantid=114606722&gad_ source=1&gclid=Cj0KCQjwir2xBh.

(Continued)

*Primary Examiner* — Alexander K Garlen

(74) *Attorney, Agent, or Firm* — Andrus Intellectual Property Law, LLP

(57) ABSTRACT

A fragrance dispenser includes a housing having a socket portion defining a receptacle for receiving a bottle of fragrance therein. A decorative cover assembly is coupled to the housing and conceals at least part of the socket portion. The decorative cover assembly comprises an outer cover and a light source positioned between the housing and the outer cover. Various illuminated effects are created by the light source and cover assembly, including a projected image (Continued)

effect, which may include timed projections, and an invisible ink effect.

12 Claims, 24 Drawing Sheets

(56)                References Cited

U.S. PATENT DOCUMENTS

| | | |
|---|---|---|
| 7,277,626 B2 | 10/2007 | Pesu et al. |
| D574,076 S | 7/2008 | Baraky |
| 7,455,444 B2 | 11/2008 | Chien |
| D628,283 S | 11/2010 | Valentino et al. |
| D633,192 S | 2/2011 | Valentino et al. |
| 7,932,482 B2 | 4/2011 | Norwood et al. |
| D647,608 S | 10/2011 | Young et al. |
| D657,040 S | 4/2012 | Young et al. |
| 8,301,019 B2 | 10/2012 | Smith et al. |
| 8,303,150 B2 | 11/2012 | Chien |
| D816,203 S | 4/2018 | Valentino et al. |
| D940,291 S | 1/2022 | Funk et al. |
| D951,420 S | 5/2022 | Funk |
| D969,290 S | 11/2022 | Guerin |
| 2005/0053368 A1* | 3/2005 | Pesu ........................ A61L 9/037 |
| | | 392/390 |
| 2006/0221594 A1* | 10/2006 | Thuot Rann ............ A61L 9/037 |
| | | 362/253 |
| 2006/0237439 A1* | 10/2006 | Norwood ............ A01M 1/2077 |
| | | 219/506 |
| 2011/0027124 A1 | 2/2011 | Albee et al. |
| 2016/0015849 A1 | 1/2016 | Lagace et al. |
| 2016/0193377 A1 | 7/2016 | Lagace et al. |
| 2021/0015955 A1 | 1/2021 | Harrell et al. |
| 2024/0261453 A1 | 8/2024 | Funk et al. |

OTHER PUBLICATIONS

Lees, Laura, Declaration of Prior Art dated Jul. 10, 2025.

* cited by examiner

FRAGRANCE DISPENSER WITH DECORATIVE COVER ASSEMBLY

CROSS-REFERENCE TO RELATED APPLICATION

This application is a continuation-in-part of U.S. application Ser. No. 18/106,762, filed Feb. 7, 2023, which is hereby incorporated by reference in its entirety.

FIELD

This invention relates to vapor emanation devices and, more particularly, to devices for diffusing one or more fragrances while at the same time providing illumination to a surrounding area.

BACKGROUND

Plug-in wick-based vapor emanation systems are known in the art for dispersing into the air vapors of a variety of liquids. Such systems are often used in the home with liquids varying from insect repellent to air freshener. Typically, in such systems, one end of a wick is partially submerged in the liquid to be dispersed. The liquid is contained in a suitable container. The partially submerged portion of the wick absorbs the liquid, some of which diffuses by capillary or wicking action into the exposed, unsubmerged portion of the wick. The exposed portion of the wick is locally heated, often by means of a heating device that fits over the wick. This causes the liquid which has diffused into the exposed portion of the wick to evaporate into the surrounding air. Continual application of heat to the exposed portion of the wick results in an evaporation/absorption process that continues until the liquid is consumed.

The below patents and publications are provided by way of background information and are hereby incorporated by reference herein in their entireties.

U.S. Pat. No. 6,236,807 discloses a vapor emanation system including a plastic housing having a socket portion and an electric plug portion. A decorative miniaturize container containing liquid to be evaporated by heat, has a body for storing the liquid and a neck connected to the body for engaging the socket portion of the housing for supporting the container on the housing. The neck has a passage there through and a retaining ring is fixed in the passage. A hole extends through the ring. A wick having an upper portion extending through the hole of the retaining ring also has a lower portion extending down into the body of the container for absorbing liquid from the container and for moving the liquid into the upper portion of the wick by capillary action. A tangential electric heater in the housing heats the upper portion of the wick above the neck to evaporate liquid from the wick. A retaining pin extending through the wick below the neck, extends radially beyond the wick by an amount which precludes upward extraction of the wick from the retaining ring to prevent a child from removing the wick and being exposed to the liquid.

U.S. Pat. No. 7,277,626 discloses an apparatus and method that combines a nightlight and an air freshener in a single device. The apparatus includes circuitry where a single resistor heats a heating block that heats and releases a volatile aromatic. The resistor also limits the current that passes through one or more light emitting diodes. The aromatic may be liquid scented oil held by a container. The container may also include a protruding wick that is heated by the heating block to facilitate oil evaporation. The light emitting diodes illuminate the housing and a decorative shield. The diodes may also illuminate fiber optic cables. The apparatus receives alternating current from a standard wall outlet. The circuitry utilized by the device ensures that the resistor is continuously powered during both half-cycles of the alternating current resulting in optimal heating of the aromatic.

U.S. Pat. No. 8,301,019 discloses a fragrance emanation system including a container for holding preferably a fragranced liquid or gel, a housing for holding the container, and a wick. The housing contains a socket for attaching to the container, a cavity for receiving the container and a door for enclosing the container. One end of the wick protrudes from the container. An electrical circuit is included having a heater for heating the protruding end of the wick and electrical connectors coupled to the circuit to receive current from a power source to provide the current to the heater. The heater heats and evaporates the liquid within the wick, thereby accelerating the emission of vapors from the evaporated liquid. The door includes a window, a bottom and a mechanism for holding the door closed to assist in holding the container in engagement with the socket.

U.S. Pat. D969,290 discloses an ornamental design for a home fragrance dispenser.

U.S. Patent Application Publication No. 2021/0015955 discloses a fragrance dispenser comprising a housing having a socket portion and defining a receptacle configured to receive a bottle having a fragrance-producing liquid therein and a wick extending therefrom. A heater can be disposed proximate to the receptacle so that, when the bottle is received within the receptacle, the heater is disposed proximate to the wick. A controller can be configured to deliver electrical voltage (e.g., pulse-width-modulated voltage) to the heater. A user input device can be in communication with the controller.

SUMMARY

This Summary is provided to introduce a selection of concepts that are further described below in the Detailed Description. This Summary is not intended to identify key or essential features of the claimed subject matter, nor is it intended to be used as an aid in limiting the scope of the claimed subject matter.

According to one embodiment of the present disclosure, a fragrance dispenser comprises a housing having a socket portion defining a receptacle configured to receive a bottle having a fragranced liquid therein and a decorative cover assembly coupled to the housing and concealing at least part of the socket portion. The decorative cover assembly comprises an outer cover and a backplate coupled to the outer cover, the backplate having a plurality of apertures formed therein. At least one film has an opaque portion and at least one translucent portion together defining at least one image, a given image of the at least one image being positioned across an aperture in the plurality of apertures. A plurality of light sources is provided, each light source in the plurality of light sources being positioned between the backplate and the outer cover and being directed at a respective aperture and the given image positioned thereacross. Light from each respective light source projects through the at least one translucent portion of the at least one film to form an illuminated version of the given image on an external surface. A controller is configured to control a first light source and a second light source of the plurality of light sources to turn on and off. The controller is configured to control the first light source to be on and the second light source to be off for a first predetermined period of time. The controller is configured to control the first and second light sources to both be on for a second predetermined period of time subsequent to the first period of time.

According to one aspect, the plurality of apertures comprises a first aperture and a second aperture, the first light source being directed at the first aperture and the second light source being directed at the second aperture. The at least one translucent portion includes a first translucent portion and a second translucent portion, wherein the first translucent portion and the opaque portion together form a first image of the at least one image positioned across the first aperture and the second translucent portion and the opaque portion together form a second image of the at least one image positioned across the second aperture. When the first light source is on and the second light source is off, light from the first light source projects through the first translucent portion to form an illuminated version of the first image on the external surface. When the first and second light sources are both on, light from the first light source projects through the first translucent portion to form an illuminated version of the first image on the external surface and light from the second light source projects through the second translucent portion to form an illuminated version of the second image on the external surface.

According to one aspect, the illuminated version of the first image and the illuminated version of the second image together form a cohesive image on the external surface.

According to one aspect, the illuminated version of the first image at least partially overlaps with the illuminated version of the second image on the external surface.

According to one aspect, the controller is configured to control the second light source to gradually increase in intensity for at least a portion of the second period of time.

According to one aspect, the controller is configured to control the first light source to be on and the second light source to be off for a third predetermined period of time subsequent to the second period of time.

According to one aspect, the decorative cover assembly further comprises a printed circuit board on which each of the light sources and the controller are held.

According to one aspect, a collar couples the decorative cover assembly to the housing.

According to one aspect, the first light source has a different color than the second light source.

According to one aspect, the illuminated version of the given image forms a scene together with the decorative cover assembly.

According to another embodiment of the present disclosure, a fragrance dispenser comprises a housing having a socket portion defining a receptacle configured to receive a bottle having a fragranced liquid therein and a decorative cover assembly coupled to the housing and concealing at least part of the socket portion. The decorative cover assembly comprises an outer cover comprising a translucent part having an inner surface facing the housing and an outer surface opposite the inner surface and at least one light source positioned between the housing and the outer cover. At least one illuminated image is visible on the outer surface of the translucent part of the outer cover when the at least one light source is on. The at least one illuminated image is not visible on the outer surface of the translucent part of the outer cover when the light source is off.

According to one aspect, a film is positioned between the light source and the outer cover, the film having an opaque portion and at least one translucent portion together defining an image. Light from the at least one light source projects through the at least one translucent portion of the film to form the at least one illuminated image on the inner surface of the translucent part of the outer cover, which is visible on the outer surface of the translucent part of the outer cover.

According to one aspect, the at least one translucent portion of the film comprises a first translucent portion and a second translucent portion. The at least one light source comprises a first light source aligned with the first translucent portion and a second light source aligned with the second translucent portion. Light from the first light source projects through the first translucent portion of the film to form a first illuminated image of the at least one illuminated image on the inner surface of the translucent part of the outer cover, which is visible on the outer surface of the translucent part of the outer cover. Light from the second light source projects through the second translucent portion of the film to form a second illuminated image of the at least one illuminated image on the inner surface of the translucent part of the outer cover, which is visible on the outer surface of the translucent part of the outer cover.

According to one aspect, a controller is configured to control the first and second light sources to turn on and off. The controller is configured to do at least one of the following: simultaneously turn the first light source on and the second light source off; simultaneously turn the first and second light sources on; and simultaneously turn the first and second light sources off.

According to one aspect, the first light source has a different color than the second light source.

According to one aspect, the at least one illuminated image is formed with ultraviolet-visible ink applied to the inner surface of the translucent part of the outer cover, and the at least one light source is an ultraviolet light source.

According to one aspect, a backplate is coupled to the outer cover, the backplate having an aperture formed therein. A film has an opaque portion and a translucent portion together defining an image, the image being positioned across the aperture in the backplate. The at least one light source comprises the ultraviolet light source and a non-ultraviolet light source. The non-ultraviolet light source is positioned between the backplate and the outer cover and is directed at the aperture and the image positioned thereacross. Light from the non-ultraviolet light source projects through the translucent portion of the film to form an illuminated version of the image on an external surface.

According to one aspect, a shield plate is positioned between the ultraviolet light source and the non-ultraviolet light source and prevents light from the non-ultraviolet light source from projecting onto the inner surface of the outer cover.

According to one aspect, a collar couples the decorative cover assembly to the housing.

Various other features, objects, and advantages of the invention will be made apparent from the following description taken together with the drawings.

BRIEF DESCRIPTION OF DRAWINGS

The present disclosure is described with reference to the following Figures. The same numbers are used throughout the Figures to reference like features and like components.

DETAILED DESCRIPTION

Figure 1:
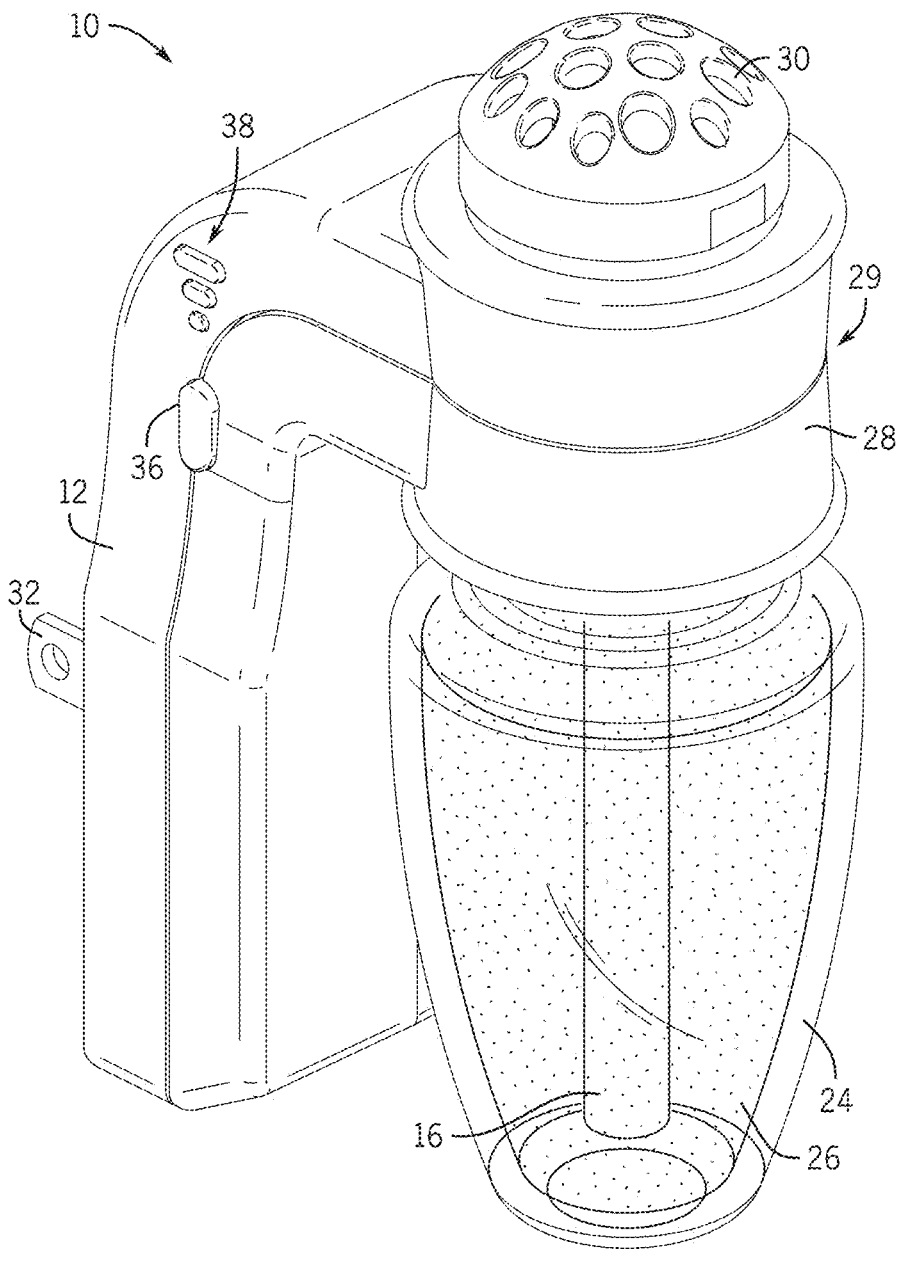
FIG. 1 is a front perspective view of a prior art fragrance dispenser.
Figure 2:
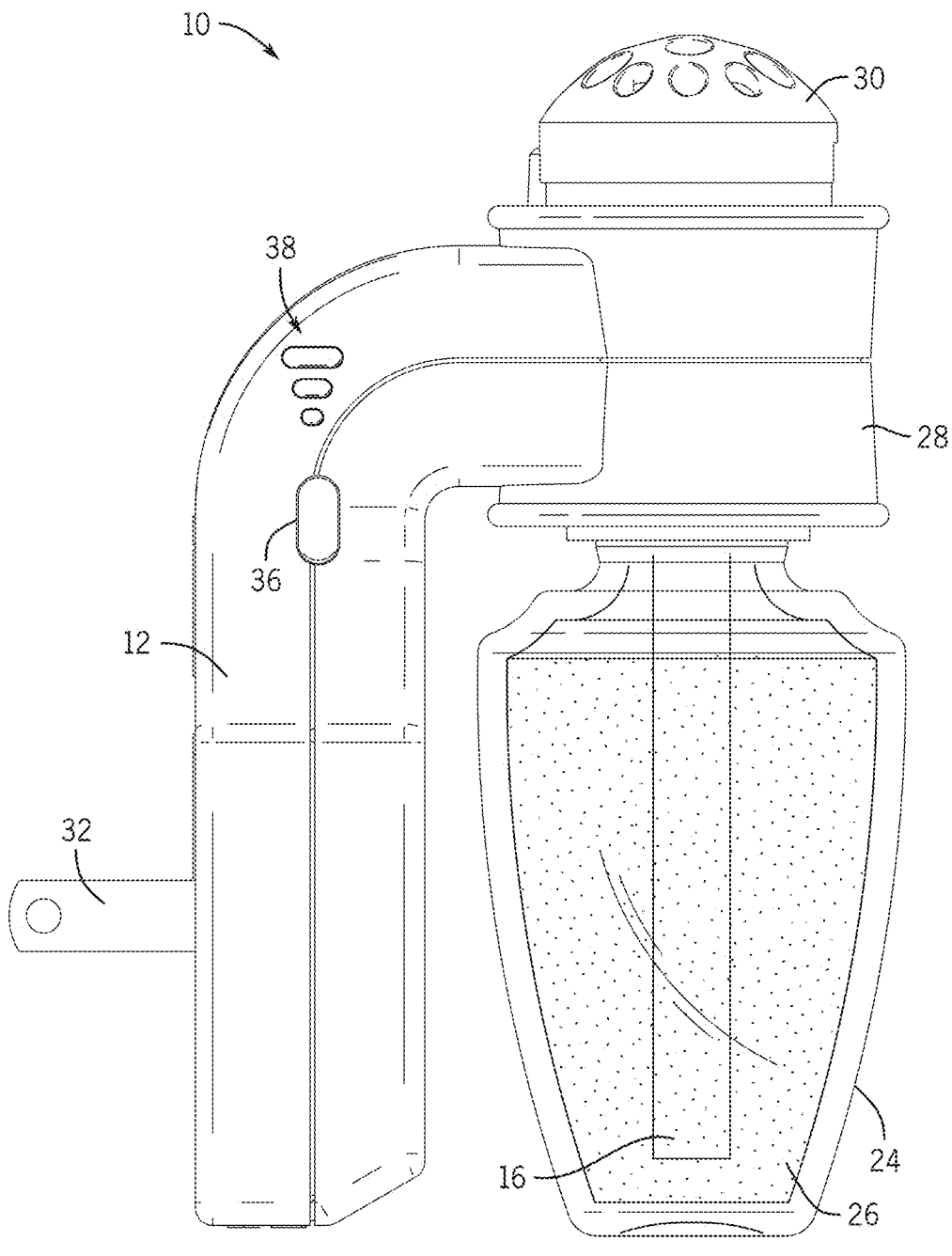
FIG. 2 is a side elevation view of the fragrance dispenser of FIG. 1.
Figure 3:
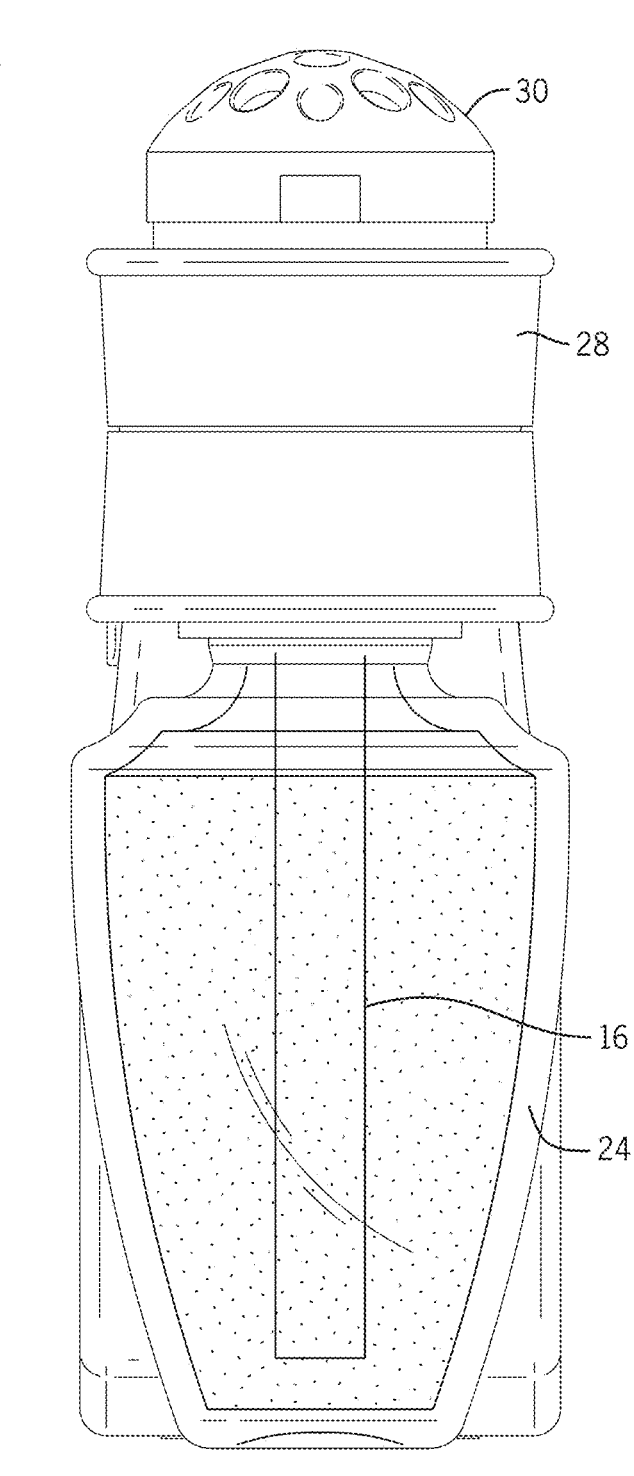
FIG. 3 is a front elevation view of the fragrance dispenser of FIG. 1.
Figure 4:
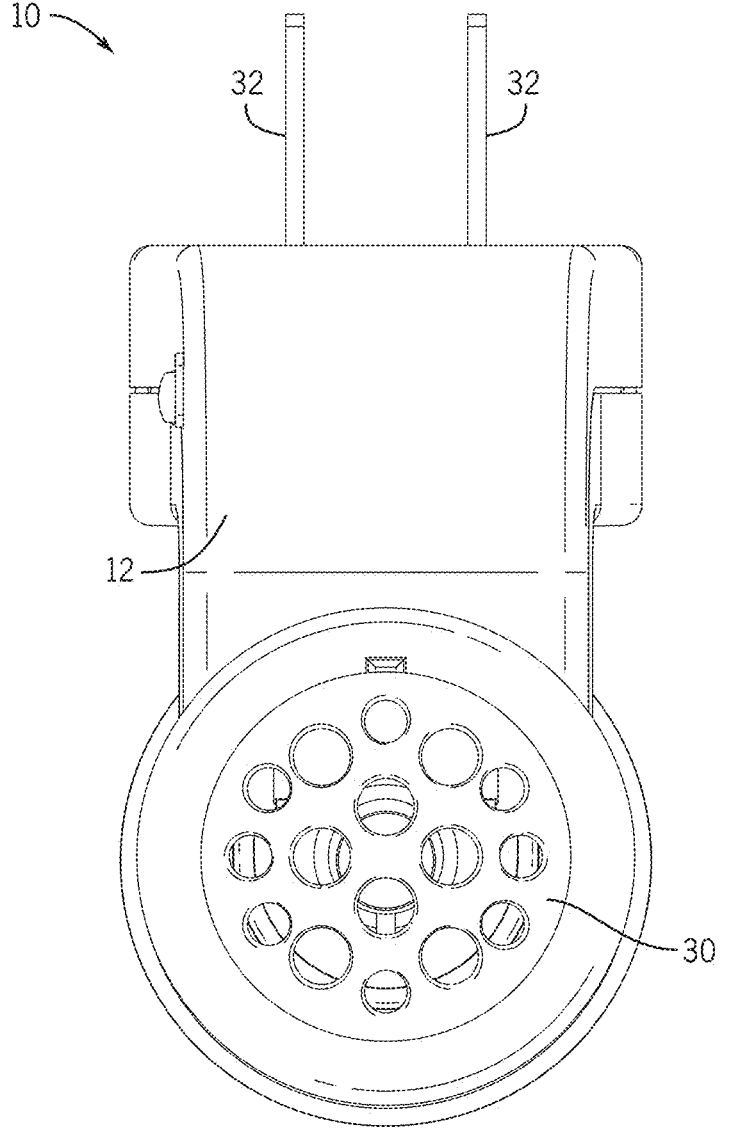
FIG. 4 is a top plan view of the fragrance dispenser of FIG. 1.

Before any embodiments of the invention are explained in detail, it is to be understood that the invention is not limited in its application to the details of construction and the arrangement of components set forth in the following description or illustrated in the drawings. The invention is capable of other embodiments and of being practiced or of being carried out in various ways. Many modifications and other embodiments of the invention set forth herein will come to mind to one skilled in the art to which the invention pertains having the benefit of the teachings presented in the following description and the associated drawings. Although specific terms are employed herein, they are used in a generic and descriptive sense only and not for purposes of limitation.

Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

Unless otherwise specified or limited, the phrases "at least one of A, B, and C," "one or more of A, B, and C," and the like, are meant to indicate A, or B, or C, or any combination of A, B, and/or C, including combinations with multiple instances of A, B, and/or C.

Unless otherwise specified or limited, the terms "mounted," "connected," "linked," "supported," and "coupled" and variations thereof are used broadly and encompass both direct and indirect mountings, connections, supports, and couplings, which may be mechanical and/or electrical.

As used herein, unless otherwise specified or limited, discussion of particular directions is provided by example only, with regard to particular embodiments or relevant illustrations. For example, discussion of "top," "bottom," "front," "back," "left," "right," "radial," "lateral" or "longitudinal" features is generally intended as a description only of the orientation of such features relative to a reference frame of a particular example or illustration. Correspondingly, for example, a "top" feature may sometimes be disposed below a "bottom" feature (and so on), in some arrangements or embodiments. Additionally, use of the words "first," "second", "third," etc. is not intended to connote priority or importance, but merely to distinguish one of several similar elements from another.

Ranges can be expressed herein as from "approximately" one particular value and/or to "approximately" another particular value. When such a range is expressed, another aspect includes from the one particular value and/or to the other particular value. Similarly, when values are expressed as approximations, by use of the antecedent "approximately," it will be understood that the particular value forms another aspect. It will be further understood that the end-points of each of the ranges are significant both in relation to the other endpoint, and independently of the other endpoint. Optionally, in some aspects, when values are approximated by use of the antecedent "approximately," it is contemplated that values within up to 15%, up to 10%, up to 5%, or up to 1% (above or below) of the particularly stated value can be included within the scope of those aspects.

Unless otherwise specified or limited, the word "majority" means more than 50%.

PRIOR ART

Figure 5:
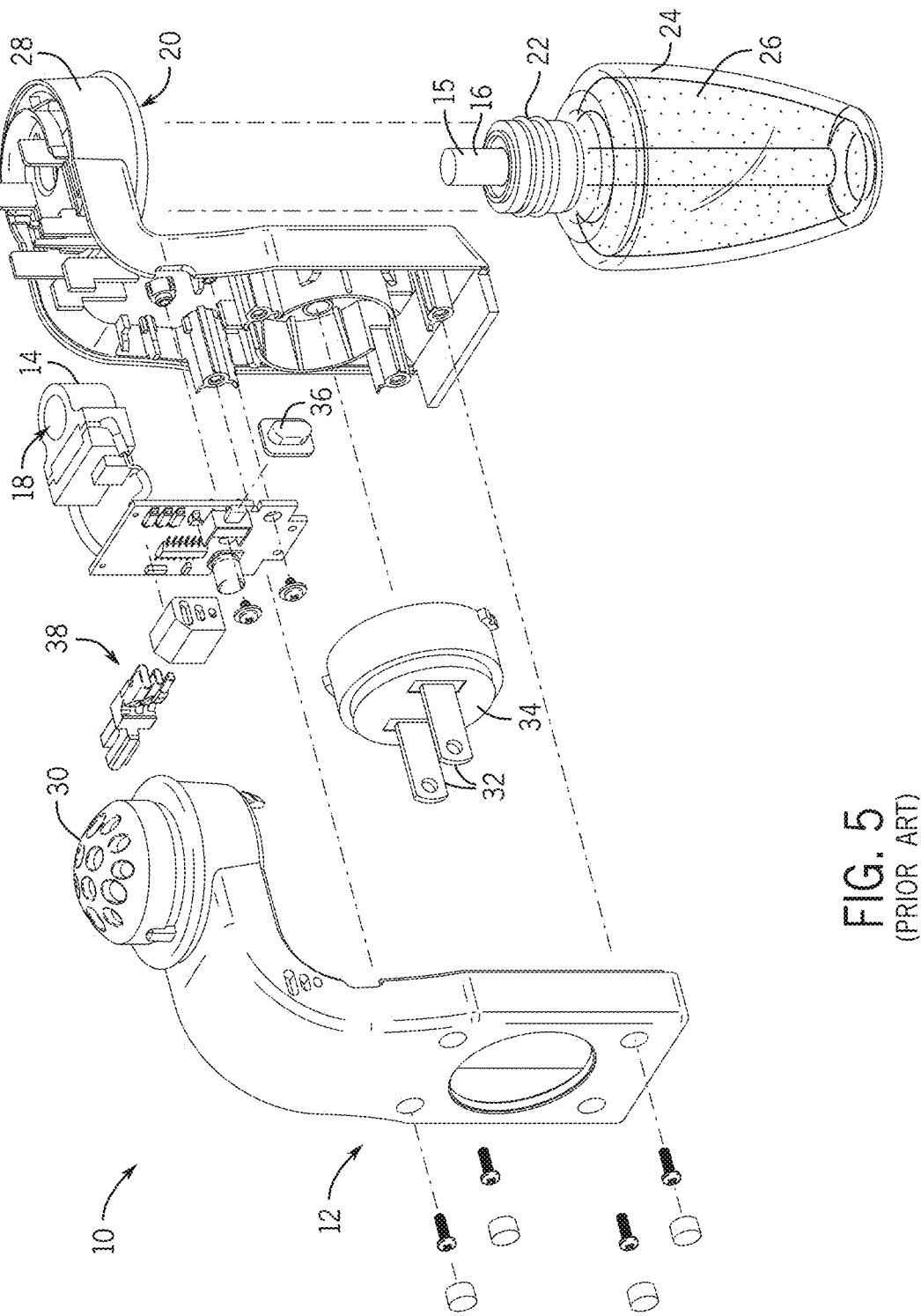
FIG. 5 is an exploded perspective view of the fragrance dispenser of FIG. 1.

A prior art fragrance dispenser 10 is shown in FIGS. 1-5. The fragrance dispenser 10 can comprise a multi-part plastic dispenser housing 12 containing a heater assembly 14 (FIG. 5) for heating an upper end 15 of a wick 16 extending from a bottle 24. The wick 16 can have a cylindrical shape (or other suitable shape) and the upper end 15 is insertable (via a central opening in a receptacle 20) into a hole 18 that extends through the heater assembly 14, as shown in FIG. 5. The dispenser's housing 12 can include a receptacle 20, which can optionally be reverse threaded, and which receives the reverse threaded neck 22 of a bottle 24 that contains a liquid 26 configured to produce an air freshening fragrance. As used herein, the term "bottle" refers to any container capable of storing a liquid that produces a fragrance as disclosed herein. It should be understood that, in some contexts, the term "fragrance" as used herein refers to the scent produced as a result of the heating and vaporization of the liquid 26. However, in other contexts, it should be understood that the terms "liquid" and "fragrance" may be used interchangeably. The wick 16 can absorb the liquid 26 and bring it to the upper end 15 by capillary action, where the liquid can be heated and vaporized by the heater assembly 14 to produce the fragrance.

As noted, the bottle 24 can comprise a reverse screw threaded neck 22 (FIG. 5). Thus, the bottle 24, when viewed from above, can be turned clockwise to tighten it into the receptacle 20 and counter-clockwise to loosen and remove it. More generally, it is contemplated that the bottle 24 can comprise any structure that permits secure engagement with the housing 12. The receptacle 20, which is formed in a socket portion 28 of the housing 12, can hold the bottle 24 in place with all but the neck 22 of the bottle 24 extending below the housing 12 and being exposed so that it can be seen. In some aspects, the housing 12 can hold only one single bottle 24. In further aspects, the housing 12 can be configured to receive and dispense fragrance from multiple bottles.

Optionally, the housing 12 can include a dome-shaped cover 30 having multiple holes forming vapor outlets for the heated fragrance. The cover 30 prevents access to the upper end 15 of the wick 16 and the heater assembly 14.

The fragrance dispenser 10 can be energized by receiving electricity through a pair of electrical plug blades 32 that are configured to be plugged into an electric wall outlet. Plug blades 32 can both supply electricity to, and support, the fragrance dispenser 10 in the wall outlet. A plug portion 34 of the housing 12 and the plug blades 32 can be made as one unit. Optionally, the plug portion 34 (with the plug blades 32) can be rotatable with respect to the remainder of the housing 12 so that a user can select the orientation of the plug blades 32 with respect to the remainder of the housing 12. In this way, the housing 12 can be oriented so that the bottle 24 hangs downwardly from the housing 12 when the plug blades 32 are plugged into the wall outlet, regardless of the orientation of the electrical socket in the wall outlet.

Figure 6:
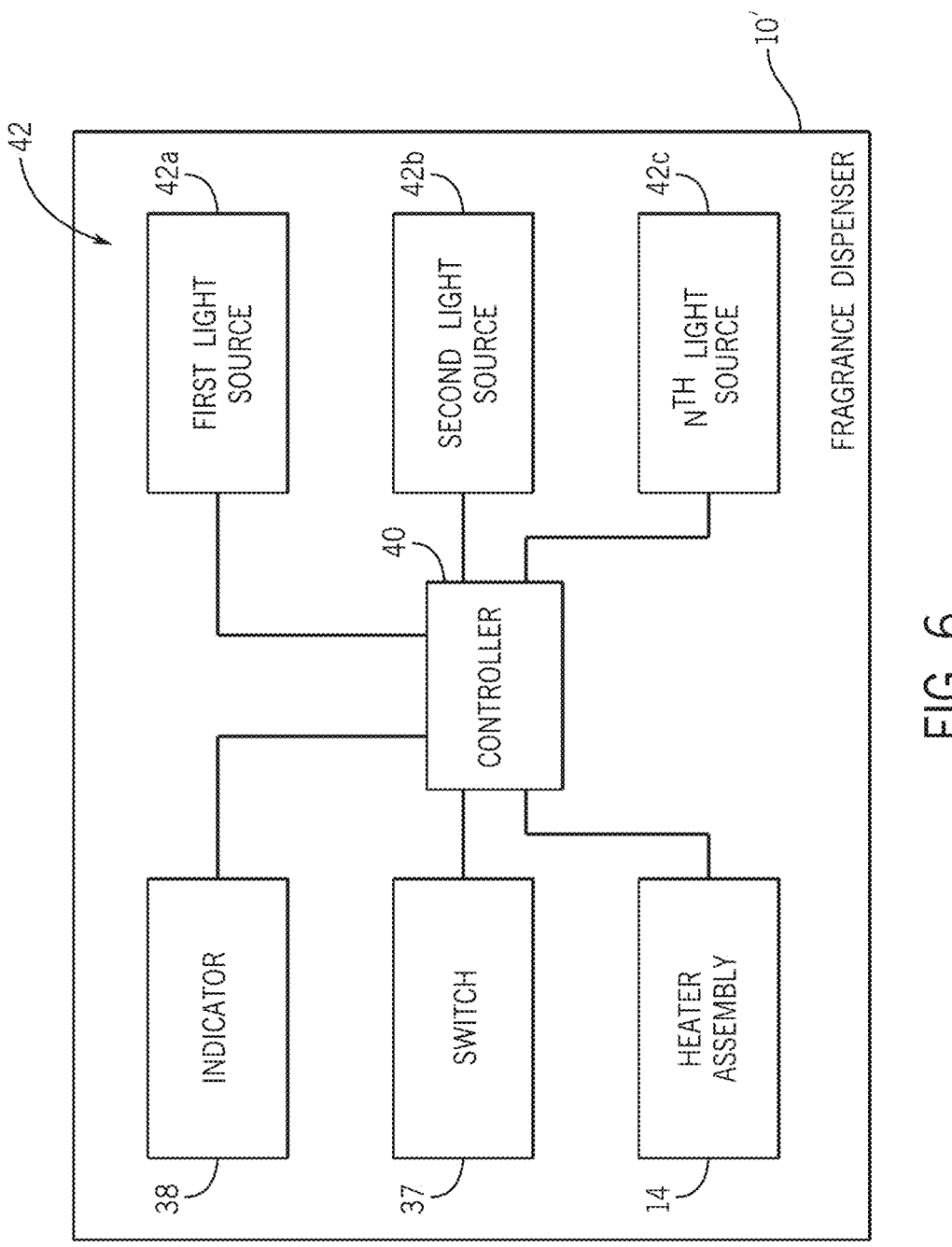
FIG. 6 is a schematic of an electrical layout of a fragrance dispenser according to the present disclosure.
Figure 7:
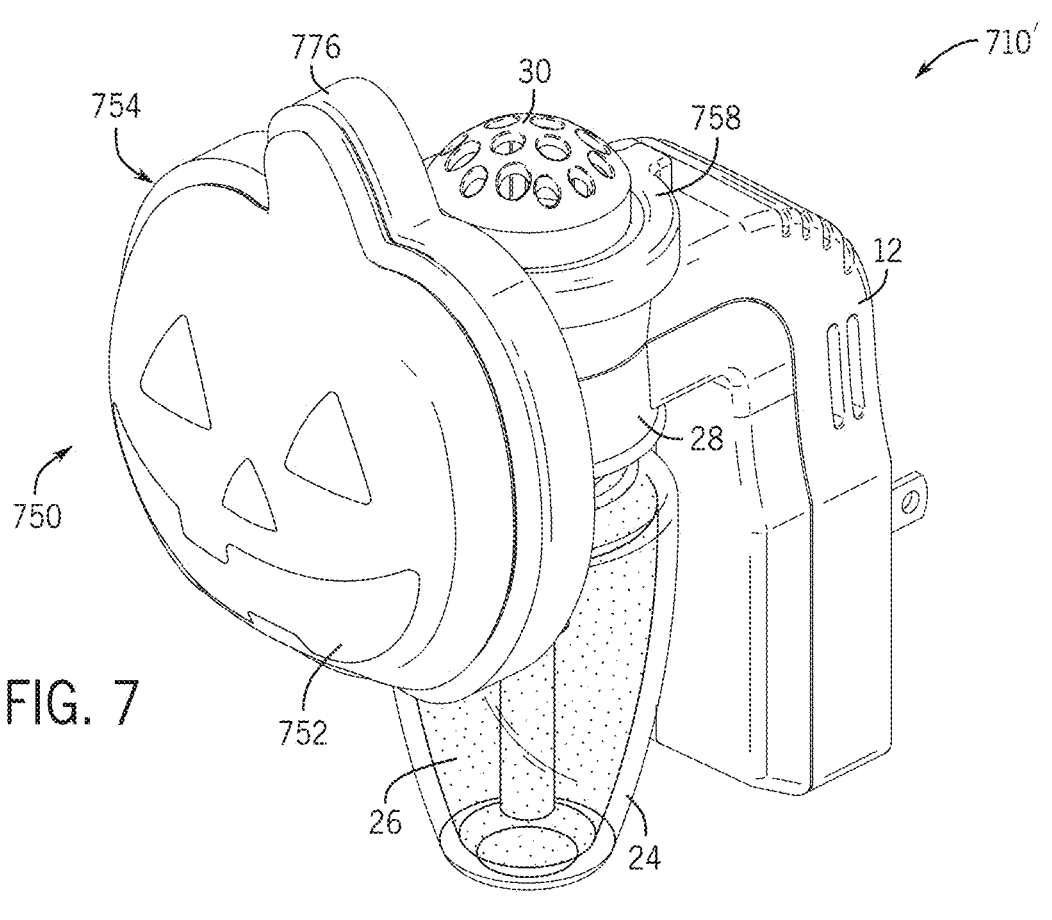
FIG. 7 is a front perspective view of a first embodiment of a fragrance dispenser.

The fragrance dispenser 10 can incorporate various other features disclosed in U.S. Pat. No. 6,236,807, incorporated by reference herein. The fragrance dispenser 10 can instead or also incorporate various other features disclosed in U.S. Patent Application Publication No. 2021/0015955, incorporated by reference herein, such as, but not limited to, a user input device (e.g., button 36) that actuates a switch 37 (FIG. 6) in communication with a controller 40 that changes the duty cycle of the PWM electric voltage delivered to the heater assembly 14. A PWM electrical voltage with a higher duty cycle can cause the fragrance dispenser 10 to dispense fragrance at a higher rate than a PWM electrical voltage with a lower duty cycle. The fragrance dispenser 10 can further comprise an illuminated indicator assembly 38 that shows the controller's duty cycle setting.

Exemplary Embodiments

The fragrance dispensers of the present embodiments comprise a housing, such as for example the prior art housing 12, and at least some of the components (although not necessarily all components) described hereinabove. In addition, the fragrance dispensers of the present embodiments comprise a decorative cover assembly coupled to the housing 12, which decorative cover assembly includes at least one light source, as will be described further herein below. Prior to detailed descriptions of the various embodiments of decorative cover assemblies, reference to FIG. 6 shall be made to explain one possible example of the electrical connections within the fragrance dispensers of the present embodiments. Each fragrance dispenser 10' includes a controller 40 in electrical communication with the heater assembly 14. The controller 40 can be a microcontroller, an ASIC, a FPGA, or any integrated circuit capable of carrying out the functions described herein. In some embodiments, the fragrance dispenser 10' can comprise at least one light source 42 (optionally, a plurality of light sources including first light source 42a, second light source 42b, and $N^{th}$ light source 42c). In some embodiments, the at least one light source 42 can comprise a light engine, such as a light emitting diode (LED). The at least one light source 42 can have an intensity that varies based on the duty cycle. For example, a high duty cycle can correspond to a high light intensity and a low duty cycle can correspond to a low light intensity. In some embodiments, the at least one light source 42 and the heater assembly 14 can be on the same circuit. That is, the same voltage can be provided to the at least one light source 42 and the heater assembly 14. In some embodiments, the at least one light source 42 can be connected in series with the heating assembly's resistor. In this way, the at least one light source 42 and heater assembly 14 can be controlled with a single controller 40, which can reduce the required size of the housing 12 and decrease overall complexity of the circuitry as compared to a device requiring separate controllers to control the at least one light source 42 and the heater assembly 14. The controller 40 can also simultaneously modulate the pulse width to the heater assembly 14 and the at least one light source 42 so that the intensity of the at least one light source 42 can vary with the fragrance output of the fragrance dispenser 10'. In still further embodiments, the at least one light source 42 can turn on or off or change color/intensity based on the duty cycle of the PWM signal passing a threshold. In still further embodiments, the status of the at least one light source 42 can change with the PWM duty cycle of the heater assembly 14. For example, if the duty cycle is above 50%, the at least one light source 42 can be illuminated, while if the duty cycle is below 50%, the at least one light source 42 can be off.

Although described herein as being connected in series with the resistor of the heater assembly 14, it is contemplated that the at least one light source 42 can also be connected with the heater assembly 14 in other configurations, such as a parallel connection. In still further embodiments, no controller is present, and the heater assembly 14 and each light source 42a, 42b, 42c are individually connected to the power source through respective resistors. In such an embodiment, the switch 37 and the indicator assembly 38 may not be present, and the fragrance dispenser may have only one level of fragrance output and one light intensity. In still further embodiments, provision of electrical power to the light sources 42 may be able to be controlled manually via a switch, independently of provision of electrical power to the heater assembly 14.

Decorative Cover Assemblies with Light Guides

The embodiments of FIG. 7-14 include decorative cover assemblies attached to the fragrance dispenser 10', which decorative cover assemblies include at least one light source and a light guide. FIGS. 7-14 disclose a fragrance dispenser 710', 910', 1110', 1310' comprising a housing 12 having a socket portion 28 defining a receptacle 20 (FIG. 5) configured to receive a bottle 24 having a fragranced liquid 26 therein. A decorative cover assembly 750, 950, 1150, 1350 is coupled to the housing 12 and conceals at least part of the socket portion 28. In each embodiment, a collar 756, 956, 1156, 1356 couples the decorative cover assembly 750, 950, 1150, 1350 to the housing 12. The collar 756, 956, 1156, 1356 includes a ring-shaped portion 758, 958, 1158, 1358 that fits over the cover 30 and is attached thereto by way of a friction fit, an interference fit, and/or adhesive. The collar 756, 956, 1156, 1356 also includes a bracket portion (e.g., 760, 1160, 1360) extending forwardly from the ring-shaped portion 758, 958, 1158, 1358 and connected to the decorative cover assembly 750, 950, 1150, 1350. The decorative cover assemblies 750, 950, 1150, 1350 can be coupled to the housing 12 in other ways than that shown in the present embodiments.

The decorative cover assembly 750, 950, 1150, 1350 comprises an outer cover 752, 952, 1152, 1352 and a light source 742, 942, 1142, 1342 positioned between the housing 12 and the outer cover 752, 952, 1152, 1352. The decorative cover assembly 750, 950, 1150, 1350 also comprises a light guide 754, 954, 1154, 1354 positioned to receive light from the light source 742, 942, 1142, 1342 and configured to direct the light to a location remote from the light source 742, 942, 1142, 1342.

"Neon" Effect Decorative Cover Assemblies

The embodiments of FIG. 7-12 include decorative cover assemblies attached to the fragrance dispenser 10 which have a "neon" effect when the at least one light source is lit. Note that neon (or another gas) is not actually used in the decorative cover assemblies shown herein; rather, light guides such as light pipes and light plates are used to create a lighted "tubular" effect around the decorative cover assembly similar to that of true neon lighting. In the embodiments of FIGS. 7-12, the remote location to which the light guide directs light is at least part of a perimeter 762, 962, 1162 of the outer cover 752, 952, 1152. Thus, the outer covers 752, 952, 1152 appear to have tubular neon lights around their perimeters 762, 962, 1162. This effect is achieved in different ways depending on the complexity of the shape of the perimeter 762, 962, 1162 of the outer cover 752, 952, 1152.

Figure 8:
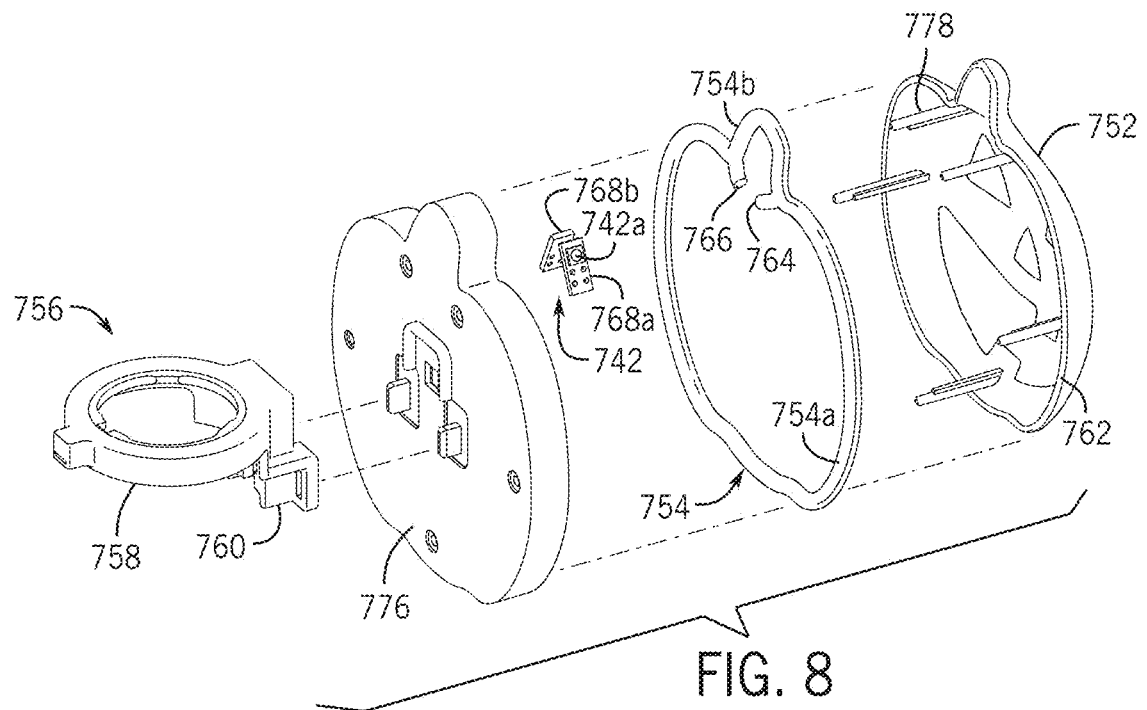
FIG. 8 is an exploded perspective view of a decorative cover assembly of the fragrance dispenser of FIG. 7.

In the examples of FIGS. 7-10, the light guide 754, 954 is a light pipe having an end positioned immediately adjacent the light source 742, 942. The light pipe is configured with a shape of the at least part of the perimeter 762, 962 of the outer cover 752, 952 and outlines the at least part of the perimeter 762, 962. For example, as shown in FIG. 8, a light pipe 754a has an end 764 positioned immediately adjacent the light source 742, more particularly a first light source 742a. The light pipe 754a has a shape of the entire perimeter 762 of the outer cover 752, which in this non-limiting embodiment is the shape of a pumpkin with a stem. Light enters the end 764 of the light pipe 754a and travels by internal reflection around the body of the pumpkin to the opposite end 766. Some of the light refracts out of the light pipe 754a, causing the light pipe 754a to be illuminated.

In some instances, the decorative cover assembly 750 further comprises an additional light source positioned between the housing 12 and the outer cover 752. For example, the light source 742 may include a second light source (not shown) supported on the face of the PCB 768b opposite that shown in in FIG. 8, similar to how the light source 742a is supported on PCB 768a. The second light source can be positioned immediately adjacent the end 766 of a second light pipe 754b such that light from the light source is directed into the end 766 and around the stem portion of the pumpkin.

Figure 9:
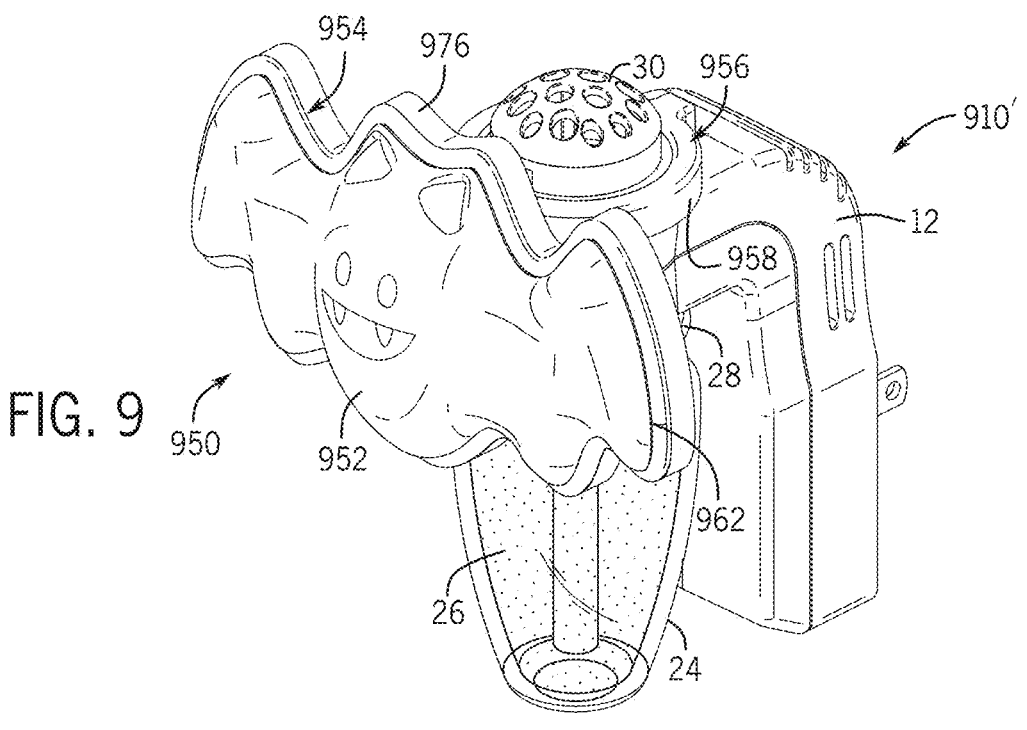
FIG. 9 is a front perspective view of a second embodiment of a fragrance dispenser.
Figure 10:
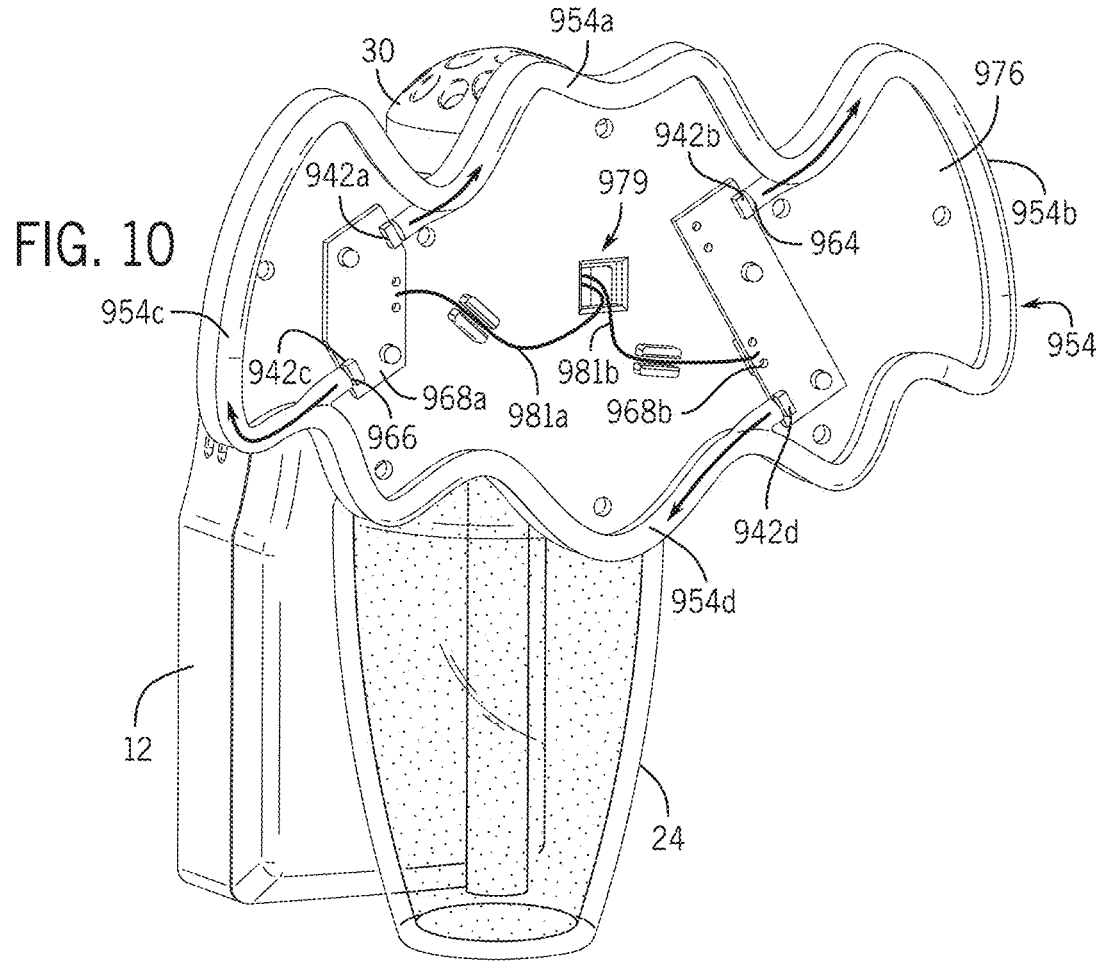
FIG. 10 is an opposite front perspective view of the fragrance dispenser of FIG. 9 with an outer cover of a decorative cover assembly removed.

Similarly, the decorative cover assembly 950 of FIGS. 9 and 10 comprises the first light source 942a and an additional light source 942b, 942c, 942d positioned between the housing 12 and the outer cover 952. The decorative cover assembly 950 also has a first light pipe 954a and an additional light pipe 954b, 954c, 954d, each having an end positioned immediately adjacent the additional light source 942b, 942c, 942d so as to receive light from the additional light source 942b, 942c, 942d. For example, light pipe 954b has its end 964 positioned immediately adjacent light source 942b, and light pipe 954c has its end 966 positioned immediately adjacent light source 942c. The end of light pipe 954d is similarly near light source 942d mounted to PCB 968b. The additional light pipe 954b, 954c, 954d is configured with a shape of another part of the perimeter 962 of the outer cover 952 (other than that about which light pipe 954a extends) and outlines the other part of the perimeter 962. Together, the light pipes 954a-d outline the entire perimeter 962 of the outer cover 952. Using multiple light pipes and light sources may be advantageous in that it allows for a relatively uniform intensity of light to refract from the light pipes around the entire perimeter 962, despite the perimeter 962 having a complex shape with many bends, like the bat shape shown in FIGS. 9 and 10. In the present embodiment, the light pipes are all one connected piece, but with several ends (entry points) into which light from multiple light sources is directed.

The outer cover 952 is removed from the assembly in FIG. 10, which thus shows how an aperture 979 in the backplate 976 allows for the passage of wires 981a, 981b therethrough. The wires 981a, 981b provide electrical communication between the power source or controller 40 (which may be located in the housing 12) and the PCBs 968a, 968b to which the light sources 942a-d are mounted. This same arrangement may be used for the embodiment of FIGS. 7 and 8.

Figure 11:
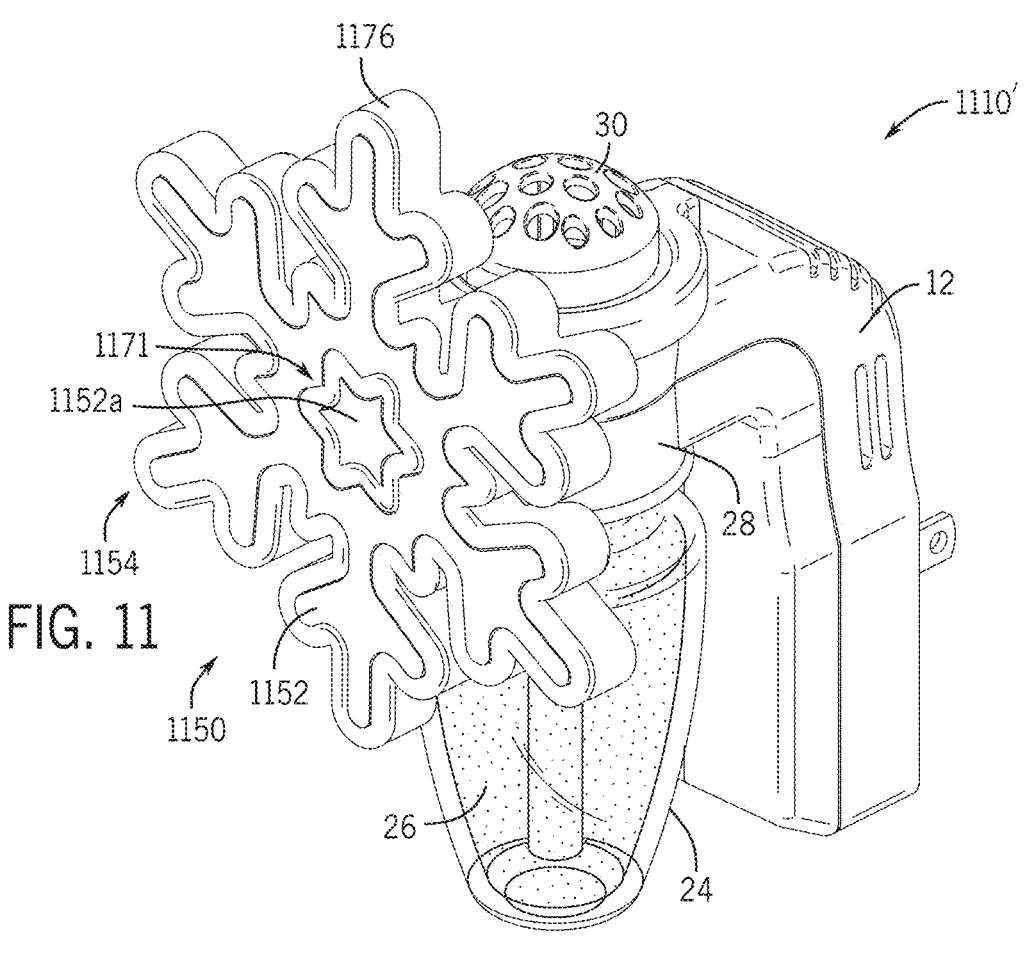
FIG. 11 is a front perspective view of a third embodiment of a fragrance dispenser.
Figure 12:
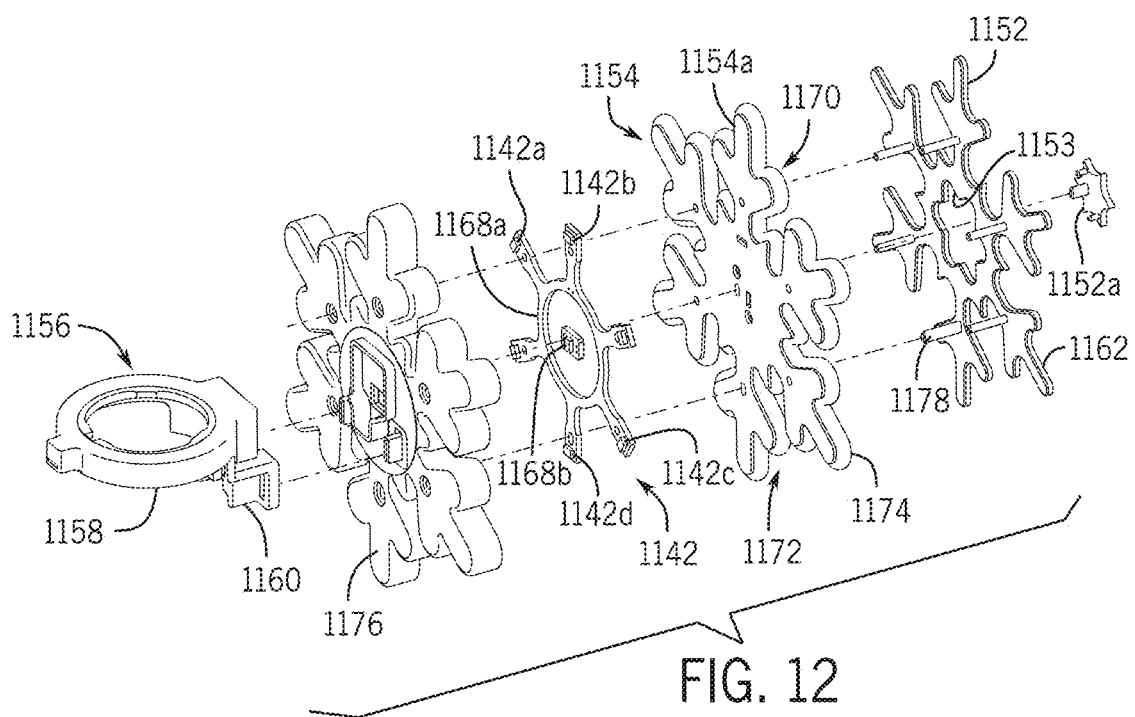
FIG. 12 is an exploded perspective view of a decorative cover assembly of the fragrance dispenser of FIG. 11.

FIGS. 11 and 12 show another example in which the remote location to which light from the light source 1142 is directed is at least part of a perimeter 1162 of the outer cover 1152. In this embodiment, however, the light guide 1154 is a light plate 1154a having a front face 1170 adjacent the outer cover 1152 and a rear face 1172 opposite the front face 1170. The rear face 1172 is positioned immediately adjacent the light source 1142, which in this case comprises multiple light sources, examples of which are shown at 1142a, 1142b, 1142c, and 1142d. Additional light sources can be provided on the remaining two arms of the PCB 1168a and on the same or another PCB 1168b to provided additional light into the light plate 1154a. Light travels to the ends of the arms of the snowflake-shaped light plate 1154a by internal reflection, and some light escapes via refraction to illuminate the light plate 1154a.

As shown, the outer cover 1152 has a shape similar to the shape of the light plate 1154a but is smaller than the light plate 1154a such that the light plate 1154a is visible about the at least part of the perimeter 1162 of the outer cover 1152 when the outer cover 1152 is centered on the light plate 1154a. In this specific example, both the light plate 1154a and the outer cover 1152 have the shape of a snowflake, with the perimeter 1162 of the outer cover 1152 being inwardly offset from the perimeter 1174 of the light plate 1154a. The front face 1170 of the light plate 1154a may be indented such that the outer cover 1152 sits flush with or even recessed from the surrounding perimeter 1174 of the light plate 1154a. The use of a light plate 1154a and an outer cover 1152 attached to the front face 1170 of the light plate 1154a may allow for the perimeter of even more complex shapes, such as the snowflake shown herein, to be outlined by light from an illuminated light guide without requiring multiple light pipes.

In the present embodiment, the outer cover 1152 comprises a cutout 1153 through which the front face 1170 of the light plate 1154a is visible. An additional cover piece 1152a can be attached within the cutout 1153 to leave an uncovered portion 1171 of the light plate 1154a, which adds a decorative effect. Although only one central cutout 1153 is shown here, additional cutouts and/or a cutout located in a different place could be provided. Alternatively, no cutout could be provided.

Each of the decorative cover assemblies 750, 950, 1150 shown in in FIGS. 7-12 further comprises a backplate 776, 976, 1176 positioned between the housing 12 and the light source 742, 942, 1142. The backplate 776, 976, 1176 in turn is what is connected to the bracket portion (e.g., 760, 1160) of the collar 756, 956, 1156 that supports the decorative cover assembly 750, 950, 1150 on the fragrance dispenser 710', 910', 1110'. In each case, the outer cover 752, 952, 1152 is connected to the backplate 776, 976, 1176, such as by way of pins (e.g., as shown at 778, 1178) on the outer cover 752, 952, 1152 that extend through corresponding apertures in the backplates 776, 976, 1176. The pins (e.g., 778, 1178) can be friction fit into the apertures, and the outer cover 752, 952, 1152 can be adhered or welded to the backplate 776, 976, 1176. In other examples, the pins 778, 978, 1178 can be thermally welded to the backplate 776, 976, 1176. Other ways to couple the outer cover 752, 952, 1152 to the backplate 775, 976, 1176 would be known to those having ordinary skill in the relevant art, and include spring arms, bonding/gluing and interference fits.

In the embodiments of FIGS. 7-12, the backplate 776, 976, 1176 supports the light source 742, 942, 1142. That is, backplate 776 supports PCBs 768a, 768b upon which light sources 742 are supported; backplate 976 supports PCBs 968a, 968b upon which light sources 942 are supported; and backplate 1176 supports PCBs 1168a, 1168b upon which light sources 1142 are supported. The light sources (such as directional LEDs) are oriented on the PCBs in a manner such that they emit light directly into the ends of the light pipes or directly at the light plate.

In some embodiments, the backplate 776, 976, 1176 is opaque. This may be desired so that the PCBs and other electronics are hidden from view. In some embodiments, the outer cover 752, 952, 1152 is also opaque. This may enhance the "neon" tube effect around the perimeter 762, 962, 1162 of the outer cover 752, 952, 1152, as the illuminated light guide 754, 954, 1154 would starkly contrast with the opaque outer cover 752, 952, 1152. In other embodiments, however, the outer cover 752, 952, 1152 may be translucent, such that some of the light from the light sources 742, 942, 1142 illuminates the body of the outer cover 752, 952, 1152 as well.

In some examples, the light guide 754, 954, 1154 is made of polycarbonate. If a colored effect is desired for the "neon" outline, the light source 742, 942, 1142 itself can be selected to output a desired color of light. Additionally or alternatively, the light guide 754, 954, 1154 can be tinted to a desired color. In some examples, in addition to the "neon" effect outline, the decorative cover assembly 750, 950, 1150 can be provided with a backlight effect by directing one or several light sources, which may be attached to the rear face of the backplate 776, 976, 1176, backward and upward over the housing 12, such that light projects onto a wall into which the fragrance dispenser is plugged.

Fiber Optic Decorative Cover Assemblies

Figures 13, 14, 14A:
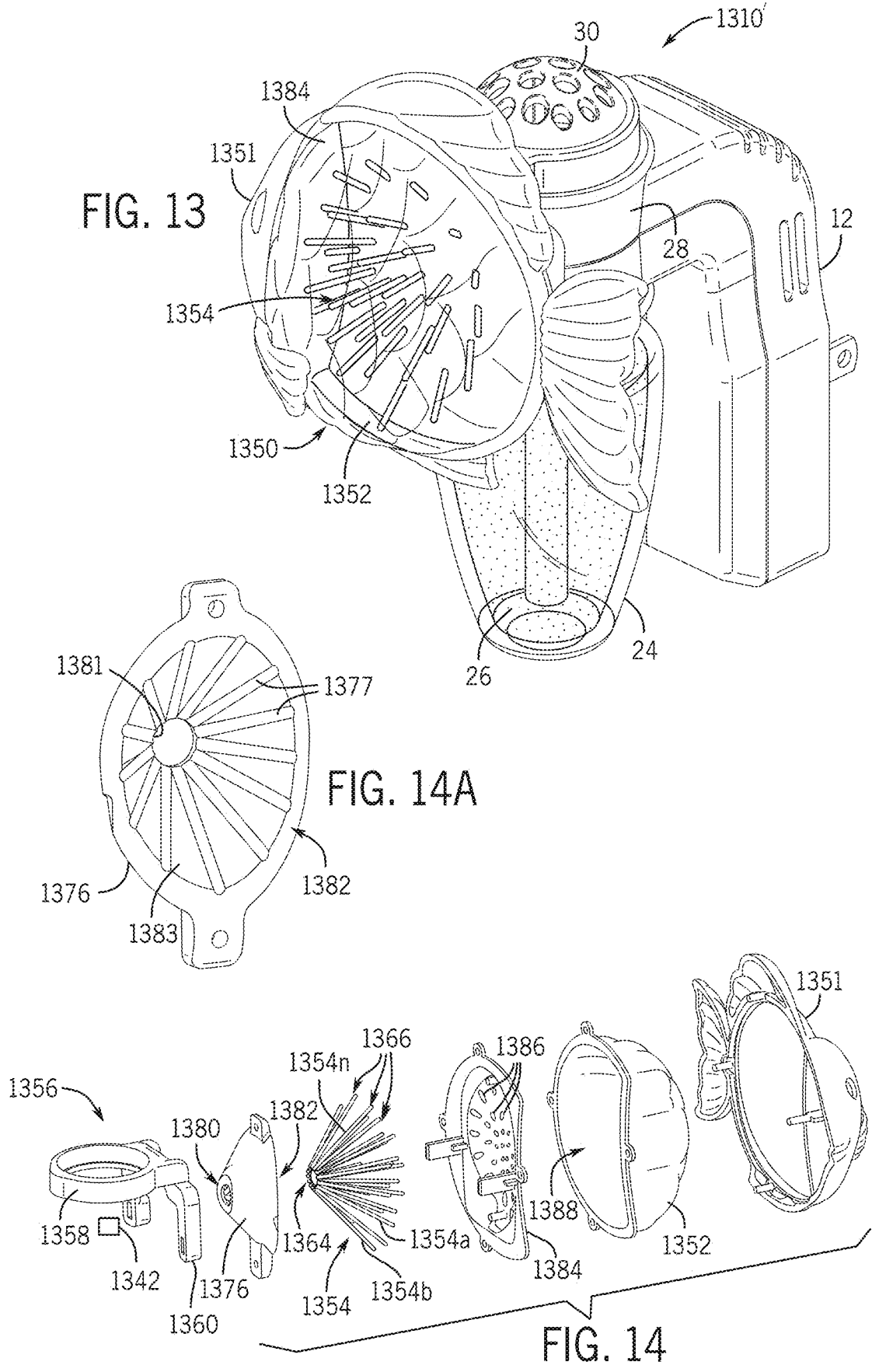
FIG. 13 is a front perspective view of a fourth embodiment of a fragrance dispenser.
FIG. 14 is an exploded perspective view of a decorative cover assembly of the fragrance dispenser of FIG. 13.
FIG. 14A is an opposite side view of a backpiece component shown in FIG. 14.

In the embodiment of FIGS. 13 and 14, the outer cover 1352 is translucent, as the light guide 1354 therein is fully covered by the outer cover 1352, as opposed to being positioned about the perimeter of the outer cover. In this embodiment, the light guide 1354 comprises a plurality of optical fibers (e.g., 1354a, 1354b . . . 1354n, where "n" is approximately 10 to approximately 50) positioned between the light source 1342 and the outer cover 1352. The light source 1342 may be located on the forward-facing surface 29 (FIG. 1) of the socket portion 28 of the housing 12. The light source 1342 can be electrically connected to the controller 40 or a resistor (in turn connected to the power source) within the housing 12 and can extend through an opening (not shown) in the forward facing surface 29 of the socket portion 28. Each optical fiber 1354a-n in the plurality of optical fibers has a first end (generally at 1364) adjacent the light source 1342 and extending toward the outer cover 1352 to a respective second end 1366. Each of the first ends 1364 are clustered together and each of the second ends 1366 are splayed apart from one another. To provide this arrangement, the decorative cover assembly 1350 further comprises a backpiece 1376 positioned between the housing 12 and the outer cover 1352, and the backpiece 1376 holds the respective first ends 1364 of the plurality of optical fibers 1354a-n. As shown in FIGS. 14 and 14A, the backpiece 1376 is frustoconical, with a smaller rear end 1380 of the backpiece 1376 being located adjacent the housing 12 and a larger front end 1382 of the backpiece 1376 being located adjacent an intermediate plate 1384. The frustoconical shape allows the first ends 1364 to be held in a cluster at the rear end 1380, and the frustoconical inner surface 1383 of the backpiece 1376 supports the optical fibers 1354a-n as they splay outwardly toward their second ends 1366. In some aspects, the optical fibers 1354a-n can be glued to the inner surface 1383 of the backpiece 1376, which may include channels 1377 for receiving and thereby spreading out the most radially outwardly located optical fibers. The rear end 1380 of the backpiece 1376, in which the first ends 1364 of the optical fibers 1354a-n are held, has a central opening 1381, such that light from the light source 1342 is directed into the first ends 1364 of each of the optical fibers 1354a-n. From there, light travels down each optical fiber 1354a-n by internal reflection and exits at the second end 1366 of the respective fiber. Some of the light may also refract out of the optical fibers 1354a-n along their length. The light source 1342 and backpiece 1376 may be configured such that the light source 1342 extends into the central opening 1381 or directly abuts the first ends 1364 of the optical fibers 1354a-n at the rear end 1380 of the backpiece 1376.

As noted, the decorative cover assembly 1350 further includes the intermediate plate 1384, which is positioned between the backpiece 1376 and the outer cover 1352. The intermediate plate 1384 has a plurality of openings 1386 therethrough, and at least one of the optical fibers 1354a-n in the plurality of optical fibers projects through a respective opening in the plurality of openings 1386. In this embodiment, one opening 1386 is provided for each optical fiber 1354a-n. However, in other embodiments, more than one optical fiber can project through a single opening. In some instances, there may be an opening or several openings in the intermediate plate 1384 through which no optical fibers extend. Supporting the optical fibers 1354a-n within the openings 1386 helps to maintain the second ends 1366 of the optical fibers 1354a-n in the splayed configuration, while the opaque intermediate plate 1384 ensures that light directly from the light source 1342 does not illuminate the inner face 1388 of the outer cover 1352. As shown in FIG. 13, a majority of each optical fiber in the plurality of optical fibers 1354a-n is located between the intermediate plate 1384 and the outer cover 1352. That is, a majority of the length of a given optical fiber is located on the outer face of the intermediate plate 1384 so as to illuminate the inner face 1388 of the outer cover 1352. Thus, the inner face 1388 of the outer cover 1352 is illuminated by light that travels from the first ends 1364 of the optical fibers 1354a-n to the second ends 1366 thereof, but not directly by the light source 1342. This provides a twinkling effect to the decorative cover assembly 1350, with multiple individual points of light behind the outer cover 1352.

The decorative cover assembly 1350 may also include a trim piece 1351 over the outer cover 1352. The trim piece 1351 includes rearwardly projecting pegs that allow it to be connected to the outer cover 1352, which in turn includes tabs, corresponding to similarly located tabs on the intermediate plate 1384 and the backpiece 1376, through which the pins extend. The intermediate plate 1384 is coupled to the bracket portion 1360 of the collar 1356 by way of additional tabs that project rearwardly from the intermediate plate 1384 and through slots in the bracket portion 1360. Other features for assembly of the decorative cover assembly 1350 will occur to those having ordinary skill in the relevant art.

Projector Decorative Cover Assemblies

The embodiments of FIGS. 15-25 all include fragrance dispensers comprising a housing 12 having a socket portion 28 defining a receptacle 20 configured to receive a bottle 24 having a fragranced liquid 26 therein. Each also includes a decorative cover assembly 1550, 2050, 2250 coupled to the housing 12 and concealing at least part of the socket portion 28. The decorative cover assembly 1550, 2050, 2250 comprises an outer cover 1552, 2052, 2252 and a backplate 1576, 2076, 2276 coupled to the outer cover 1552, 2052, 2252. Each backplate 1576, 2076, 2276 has a plurality of apertures 1590, 2090, 2290 formed therein. Each decorative cover assembly 1550, 2050, 2250 also includes a plurality of light sources (discussed further below) positioned between the backplate 1576, 2076, 2276 and the outer cover 1552, 2052, 2252 and directed at the backplate 1576, 2076, 2276, with different resulting effects as described further herein below.

Backplates with Tooled Apertures

The embodiments of FIGS. 15-21 include backplates 1576, 2076 with apertures 1590, 2090 forming images set directly in the backplate 1576, 2076. The apertures 1590, 2090 can be tooled into the backplate after the backplate is formed or made during molding of the backplate 1576, 2076. In each embodiment, a collar 1556, 2056 couples the decorative cover assembly 1550, 2050 to the housing 12.

As shown in FIGS. 15-19, the backplate 1576 includes three apertures 1590a, 1590b, 1590c in the plurality of apertures 1590. Different shapes, sizes, and configurations for the plurality of apertures 1590 are contemplated within the scope of the present embodiment. A plurality of light sources 1542 (FIG. 18) are positioned between the backplate 1576 and the outer cover 1552 and directed at the backplate 1576 so as to project light through the plurality of apertures 1590. The plurality of light sources 1542 are shown in in FIG. 18, in which the backplate 1576 of the decorative cover assembly 1550 has been removed to show the rear face 1588 of the outer cover 1552. The decorative cover assembly 1550 further comprises a printed circuit board 1568 on which each of the light sources (e.g., LEDs) is held. PCB 1568 is in turn attached to the rear face 1588 of the outer cover 1552. Electrical power may be connected to the PCB 1568 via wires originating in the housing 12. Here, the plurality of light sources 1542 includes a first light source 1542a, which may be a pink LED; a second light source 1542b, which may be a yellow LED; and a third light source 1542c, which may be a blue LED. Although light from the first light source 1542a has a different color than light from the second light source 1542b, and each of the first and second light sources 1542a, 1542b has a different color from the third light source 1542c, in other embodiments one or more of the light sources 1542 have the same color, the intensity of which may be same for each light source or which may vary. In other embodiments, different numbers and/or colors of light sources may be provided, and the light sources may be located on a single PCB 1568 or on multiple PCBs. The colors of the LEDs described herein are merely exemplary and could vary. In other examples, the LEDs may be white LEDs and a colored filter or lens could be placed over the LED to provide a desired color.

Figure 19:
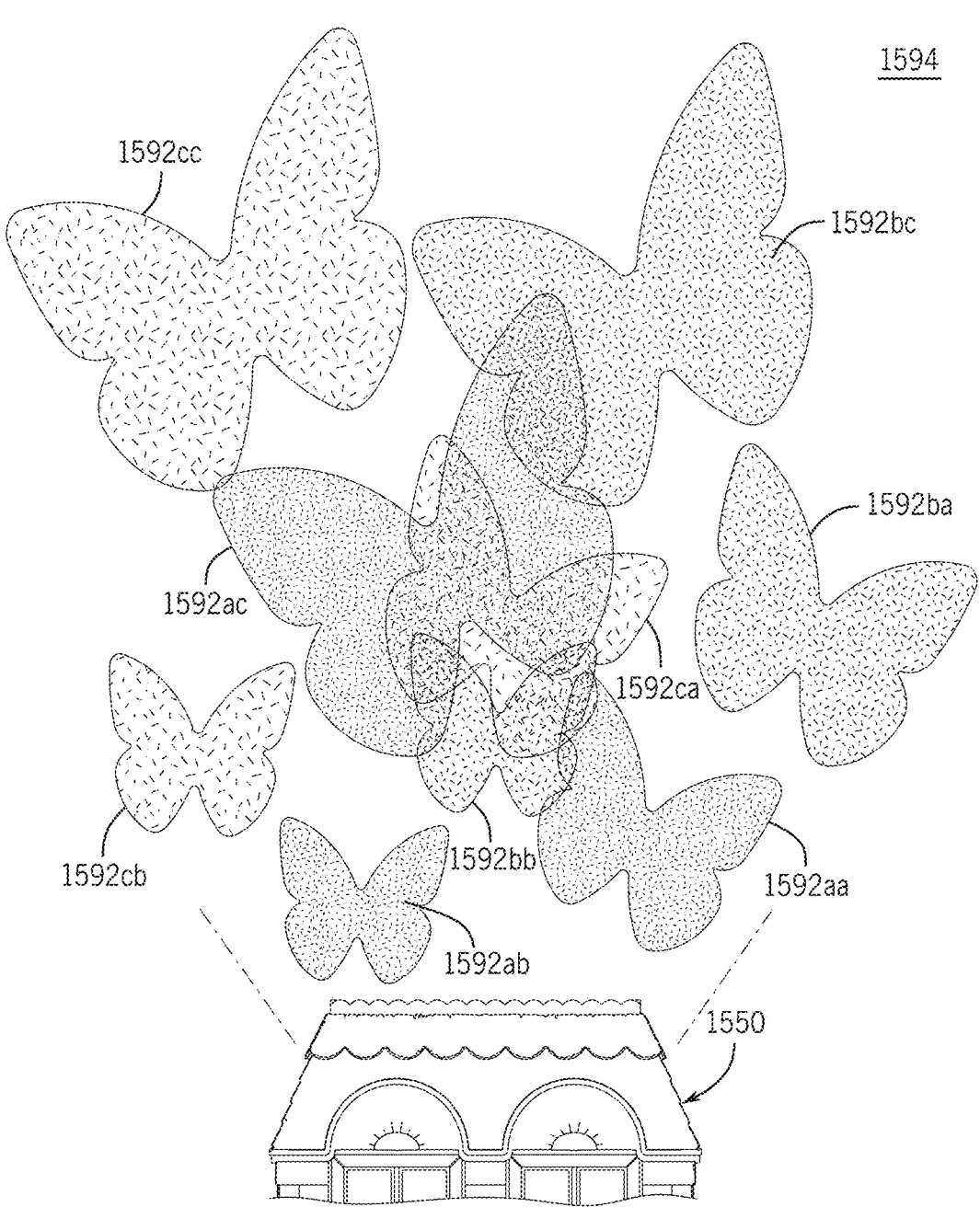
FIG. 19 shows an illuminated effect created by the fragrance dispenser of FIG. 15.

As shown in FIG. 19, light from a first light source 1542a (which in this example is pink) in the plurality of light sources 1542 projects through a first aperture 1590a in the plurality of apertures 1590 to form a first illuminated shape 1592aa on an external surface 1594 (e.g., a wall into which the fragrance diffuser is plugged). Light from a second light source 1542b (which in this example is yellow) in the plurality of light sources 1542 projects through a second aperture 1590b in the plurality of apertures 1590 to form a second illuminated shape 1592bb on the external surface 1594. At least part of the first illuminated shape 1592aa overlaps with at least part of the second illuminated shape 1592bb on the external surface 1594. In fact, in the present embodiment, light from the first light source 1542a projects from multiple apertures 1590a-c in the plurality of apertures 1590, including the first aperture 1590a, to form a first set of illuminated shapes 1592aa, 1592ab, 1592ac, including the first illuminated shape 1592aa, on the external surface 1594. So too does light from the second light source 1542b project from multiple apertures 1590a-c in the plurality of apertures 1590, including the second aperture 1590b, to form a second set of illuminated shapes 1592ba, 1592bb, 1592bc, including the second illuminated shape 1592bb, on the external surface 1594. As shown, at least part of at least one illuminated shape (e.g., 1592ac) in the first set of illuminated shapes 1592aa, 1592ab, 1592ac besides the first illuminated shape 1592aa overlaps with at least part of at least one illuminated shape (e.g., 1592bc) in the second set of illuminated shapes 1592ba, 1592bb, 1592bc besides the second illuminated shape 1592bb.

In the present embodiment, the third light source 1542c also projects through the apertures 1590a, 190b, 1590c to form illuminated shapes 1592ca, 1592cb, 1592cc on the external surface 1594. These illuminated shapes 1592ca, 1592cb, 1592cc also partially overlap with some of the illuminated shapes 1592aa, 1592ab, 1592ac, 1592ba, 1592bb, 1592bc. In fact, in the case of illuminated shapes 1592bb, 1592aa, 1592ca, and 1592ac, shapes created by all three of the light sources 1542a-c partially overlap one another.

The exemplary overlap of the illuminated shapes as shown here may be accomplished by placement of the light sources 1542a-c in a triangle on the PCB 1568, with each light source being spaced by approximately 10 mm to approximately 15 mm from the others. In other embodiments, the light sources may be vertically or horizontally aligned with one another. In other embodiments, the light sources 1542a-c may each be angled in a different direction and/or may be mounted closer to or further from the plurality of apertures 1590 in the backplate 1576 so as to change the amount of overlap of the illuminated shapes on the external surface 1594. The size, shape, and spacing of the apertures in the plurality of apertures 1590 can also be modified to create a desired overlapping effect. In the present embodiment, an upper portion 1577 of the backplate 1576 is angled outwardly away from the housing 12 (see FIG. 17) so as to project the illuminated shapes on the external surface 1594 above the housing 12 and decorative cover assembly 50, which outward angle may also affect the amount of overlap of the illuminated shapes. In one example, the angle of the upper portion 1577 of the backplate 1576 with respect to vertical is between approximately 5 degrees and approximately 10 degrees, and preferably is approximately 8 degrees. In some examples, the PCB 1568 on which the light sources 1542 are mounted is parallel to the angled upper portion 1577 of the backplate 1576. In other words, the PCB 1568 is also mounted at an angle of approximately 5-10 degrees, and preferably approximately 8 degrees, from vertical, which may be accomplished using a gusset or supporting wedge between the PCB 1568 and the rear face 1588 of the outer cover 1552.

Figure 17:
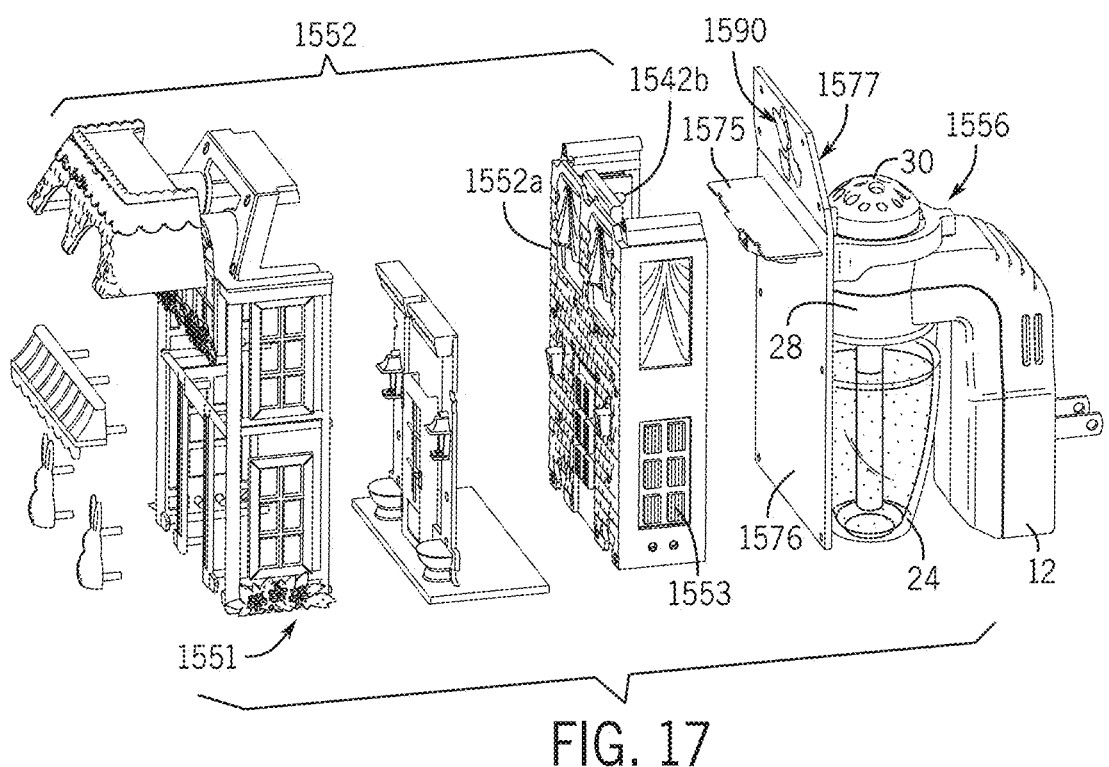
FIG. 17 is an exploded perspective view of the fragrance dispenser of FIG. 15.
Figure 18:
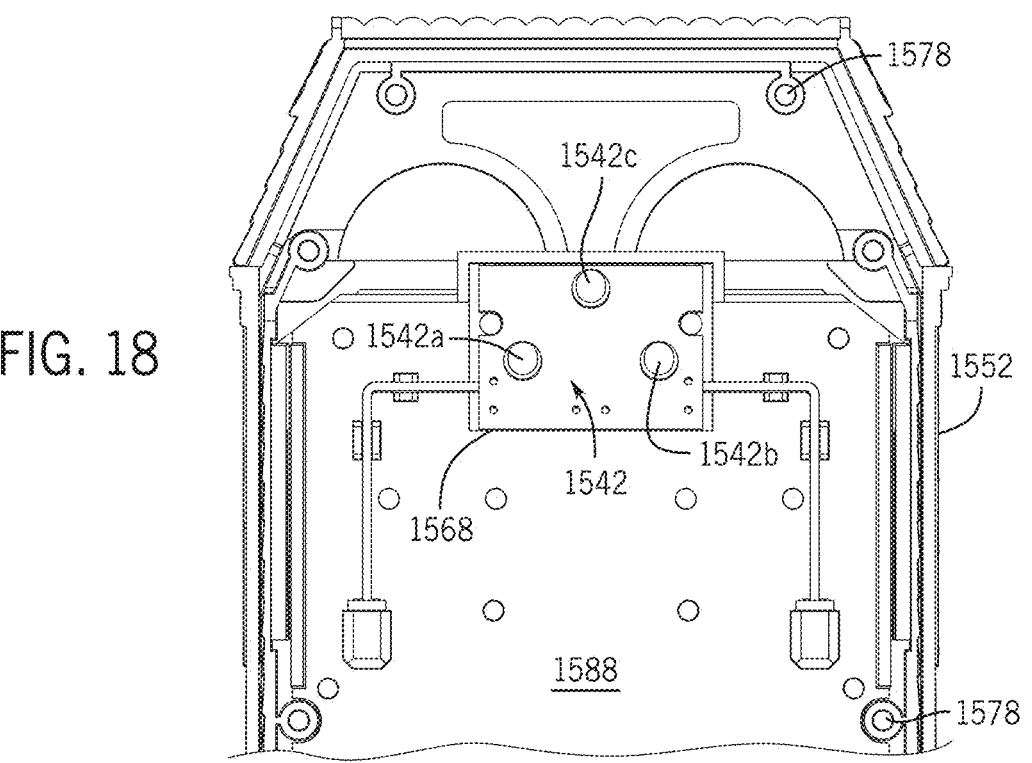
FIG. 18 is a rear elevation view of an upper portion of the decorative cover assembly of FIG. 16, with a backplate thereof removed.

Referring to FIG. 17, a ledge 1575 that projects forwardly from the front face of the backplate 1576 may be located just below the upper portion 1577 of the backplate 1576. The PCB 1568 and thus the plurality of light sources 1542 are located above the ledge 1575, which extends from the backplate 1576 to the rear face 1588 of the outer cover 1552. Thus, the ledge 1575 prevents light from the plurality of light sources 1542 from affecting illumination of other areas of the decorative cover assembly 1550, such as windows 1553 or other transparent or translucent portions of the outer cover 1552.

Figures 15, 16:
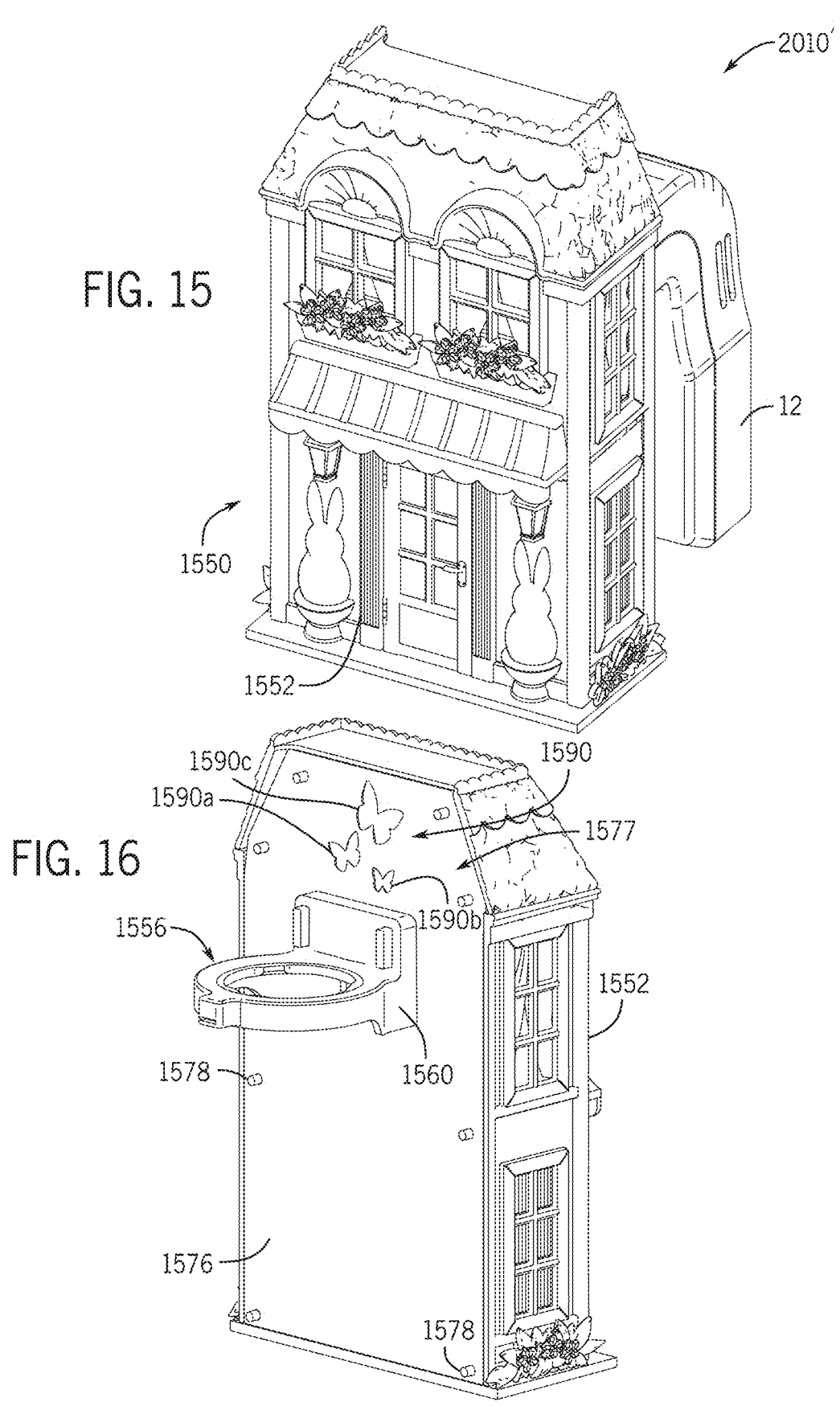
FIG. 15 is a front perspective view of a fifth embodiment of a fragrance dispenser.
FIG. 16 is a rear perspective view of a decorative cover assembly of the fragrance dispenser of FIG. 15.

The outer cover 1552 may include trim pieces 1551 that may be glued and/or snapped to the main body 1552a of the outer cover 1552. The main body 1552a of the outer cover 1552 is attached to the backplate 1576 by way of pegs (e.g., 1578, FIGS. 16, 18) on the trim pieces 1551 that extend through receiving holes in the main body 1552a and the backplate 1576 and are held in place by interference/friction fit, adhesive, and/or thermal welding. As shown in FIG. 16, the collar 1556 is attached to the backplate 1576 by way of tabs on the rear face of the backplate 1576 that extend through receiving slots in the bracket portion 1560 of the collar 1556.

Figures 20, 21:
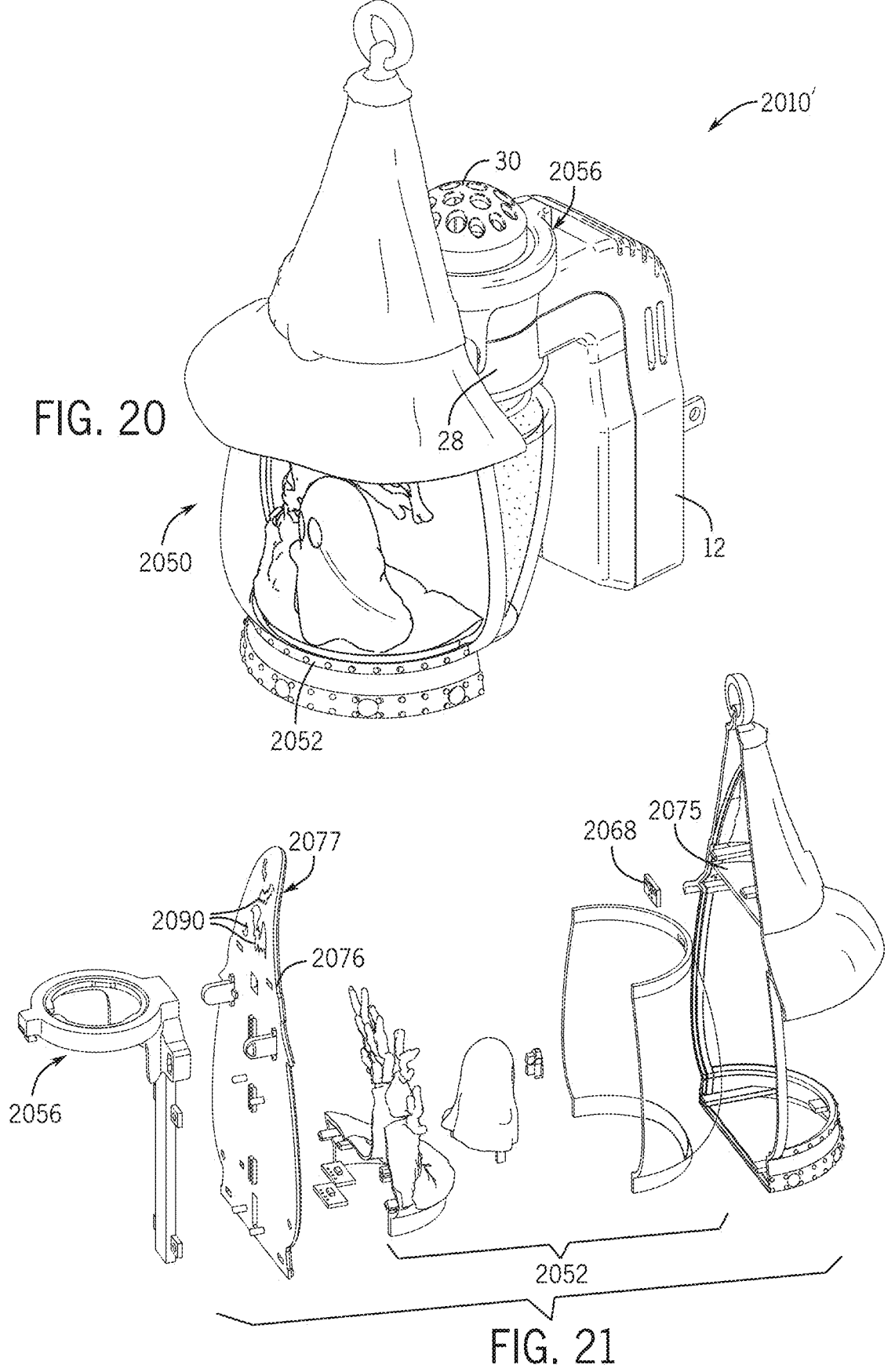
FIG. 20 is a front perspective view of a sixth embodiment of a fragrance dispenser.
FIG. 21 is an exploded perspective view of a decorative cover assembly of the fragrance dispenser of FIG. 20.
Figure 22:
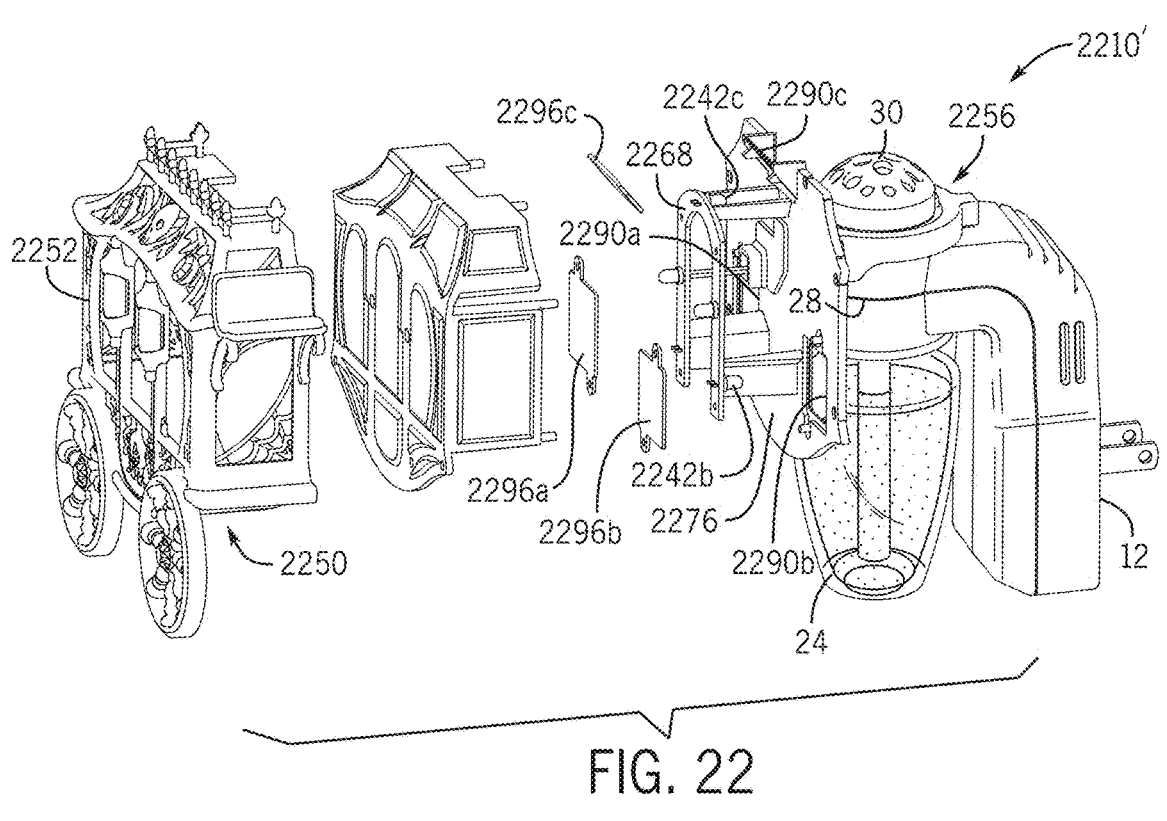
FIG. 22 is an exploded perspective view of a seventh embodiment of a fragrance dispenser.
Figure 23:
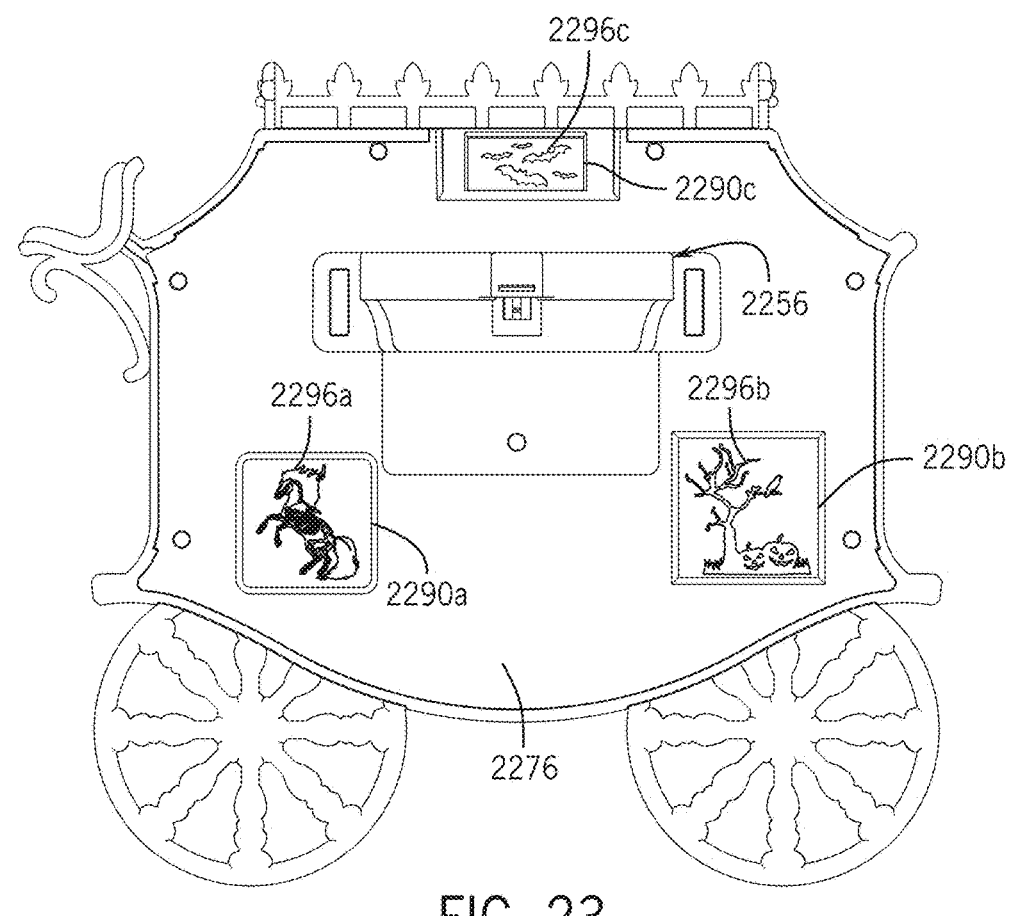
FIG. 23 is a rear elevation view of a decorative cover assembly of the fragrance dispenser of FIG. 22.

FIGS. 20 and 21 show an embodiment of a decorative cover assembly 2050 in which an upper portion 2077 of the backplate 2076 is sloped outwardly away from the housing 12, which may similarly cause the illuminated images to be projected on the external surface above the housing 12 and decorative cover assembly 2050, as well as affect the amount of overlap of the projected illuminated images. A best fit line from the bottom of the upper portion 2077 to the top of the upper portion 2077 may be angled approximately 5-10 degrees, and preferably approximately 8 degrees, from vertical. Aesthetics aside, other components of the embodiment of FIGS. 20 and 21 are similar to those described with respect to FIGS. 15-19 that are identified with the same numbers in the tens and ones places and will therefore not be described further herein. One distinction may be that the PCB 2068 may not be angled with respect to vertical, as the upper portion 2077 of the backplate 2076 is gradually sloped instead of angled. In other embodiments, the PCB 2068 may be angled with respect to vertical at an angle of approximately 5-10 degrees, and preferably approximately 8 degrees, from vertical.

The distance of the backplate 1576, 2076 from the external surface (e.g., wall) will have an effect on the size of the illuminated shapes and thus their amount of overlap. In the present embodiments, because the fragrance dispensers 1510', 2010' are intended to be plugged into an electrical socket in a wall, the distance between the backplate 1576, 2076 and the external surface is approximately 3 inches to approximately 6 inches. In other instances, if the fragrance dispenser is a standalone battery-operated unit, the size and spacing of the apertures 1590, 2090 and the size and spacing of the light sources may need to be designed appropriately to create the intended illuminated effect on an external surface that is further away.

In other embodiments, there is only a single aperture in the backplate 1576, 2076. The multiple light sources project through the single aperture in the backplate 1576, 2076 to create a pattern on the wall of overlapping illuminated versions of the shape defined by the single aperture.

Backplates with Printed Film(s)

Figures 24, 25:
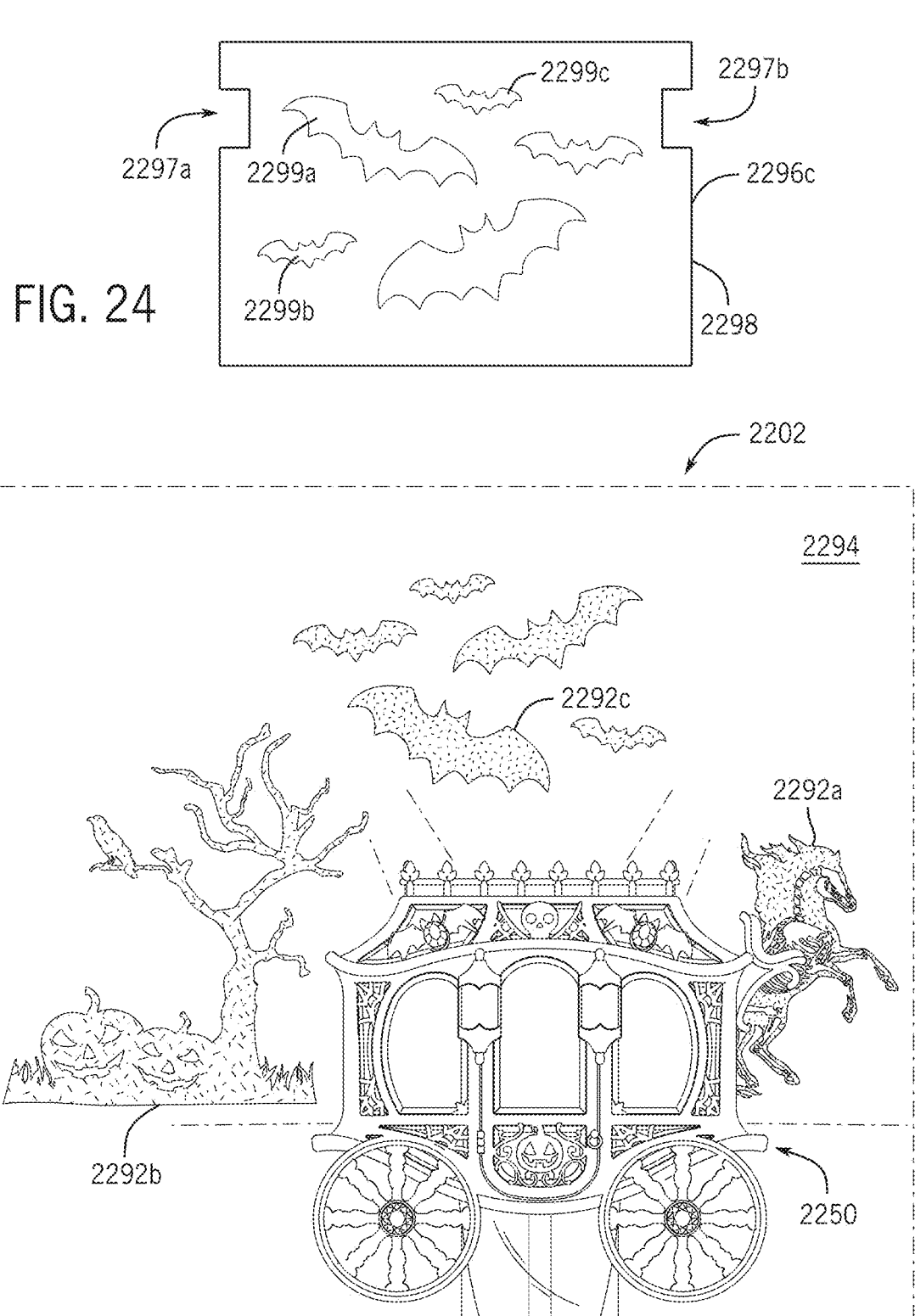
FIG. 24 illustrates a film included in the decorative cover assembly of FIG. 23.
FIG. 25 shows an illuminated effect created by the fragrance dispenser of FIG. 22.

FIGS. 22-25 show an embodiment of a fragrance dispenser 2210' having a housing 12 and a decorative cover assembly 2250 including an outer cover 2252 and a backplate 2276 as noted briefly hereinabove. A collar 2256 couples the decorative cover assembly 2250 to the housing 12. In this instance, the plurality of apertures formed in the backplate 2276 includes three apertures 2290a, 2290b, 2290c that are spaced further apart from one another than the apertures 1590, 2090 in the prior noted examples of FIGS. 15 and 20. In this embodiment, the decorative cover assembly 2250 also includes at least one film 2296a, 2296b, 2296c positioned across an aperture 2290a, 2290b, 2290c in the plurality of apertures. Referring to FIG. 24, the film 2296c located in the aperture 2290c at the top of the backplate 2276 is shown in detail. The film 2296c has at least one opaque portion 2298 and at least one translucent portion 2299a, 2299b, 2299c, etc., which opaque and translucent portions together define at least one image (here, of several bats). The films 2296a, 2296b are not shown in detail, but the same description applies thereto—i.e., each film 2296a, 2296b, 2296c has at least one opaque portion and at least one translucent portion together defining an image. Here, each image is unique to each respective film, but in other embodiments two or more of the images could be the same. In still other embodiments, multiple translucent and opaque portions could be provided on a single film that covers two or more of the apertures, with a given image formed by a given combination of translucent and opaque portions being aligned with a given aperture.

The films 2296a, 2296b, 2296c may be held in the respective apertures 2290a, 2290b, 2290c in different ways. In some embodiments, the films 2296a, 2296b, 2296c are held in place by an interference fit, such as by way of cutouts 2297a, 2297b in the outer perimeter of the film 2296c that interface with corresponding projections in the perimeter of the aperture 2290c. In other embodiments, the films may be adhered to the front face of the backplate 2276 or may be held in slots formed in the perimeter of the apertures. Other ways of maintaining the films in the apertures without interfering with the transmission of light from the light sources through the transparent portions of the films will be apparent to those having ordinary skill in the relevant art. Similar devices could be used to hold the at least one film that covers two or more of the apertures to the backplate 2276.

The decorative cover assembly 2250 also includes a plurality of light sources (e.g., 2242b, 2242c) and a PCB 2268 on which each of the light sources is held. Each light source in the plurality of light sources is positioned between the backplate 2276 and the outer cover 2252 and is directed at a respective aperture 2290b, 2290c and the given image positioned thereacross. The light source directed at aperture 2290a cannot be seen from these views, but it is located on the opposite end of the PCB 2268 from that to which light source 2242b is attached, adjacent the aperture 2290a and directed at film 2296a. Light from each respective light source projects through the translucent portion (e.g., 2299a-c) of the at least one film 2296a, 2296b, 2296c to form an illuminated version of the given image 2292a, 2292b, 2292c on an external surface 2294, as shown in FIG. 25. In the present example, each light source has a different color than the other light sources in the plurality of light sources, such that a first illuminated image 2292a is a different color from a second illuminated image 2292b, and both the first and second images 2292a, 2292b are a different color than a third illuminated image 2292c. In other examples, two or more of the illuminated images could have the same color.

Using film(s) to create the illuminated images allows for complex and detailed images to be projected onto the external surface 2294. Using the film(s) also allows for images having non-illuminated sections within illuminated sections, as the opaque portion(s) are printed onto a solid film that extends across the aperture. In preferred embodiments, the film can be any suitable transparent polymer, which may be rigid or flexible. The opaque portion(s) can be pad printed onto the film using known techniques.

In the embodiment shown in FIG. 25, the illuminated versions of the images 2292a, 2292b, 2292c form a scene 2202 together with the decorative cover assembly 2250. That is, the illuminated image 2292a of a horse appears to be pulling the carriage-shaped outer cover 2252, the carriage-shaped outer cover 2252 appears to have just passed a haunted woods represented by the illuminated image 2292b, and the illuminated image 2292c of bats appears in the "air" above the carriage. In other examples, the illuminated images do not form a scene with the decorative cover assembly 2250.

In still other examples, decorative cover assembly 2250 includes a single aperture with a single film having an opaque portion and a translucent portion together defining an image. In still other examples, decorative cover assembly 2250 includes a plurality of apertures with a single film that covers each aperture in the plurality of apertures. In the latter examples, the opaque and translucent portions that together define images are spaced on the single film such that they align with respective apertures in the plurality of apertures.

Timed Illuminated Images

Figures 26, 27:
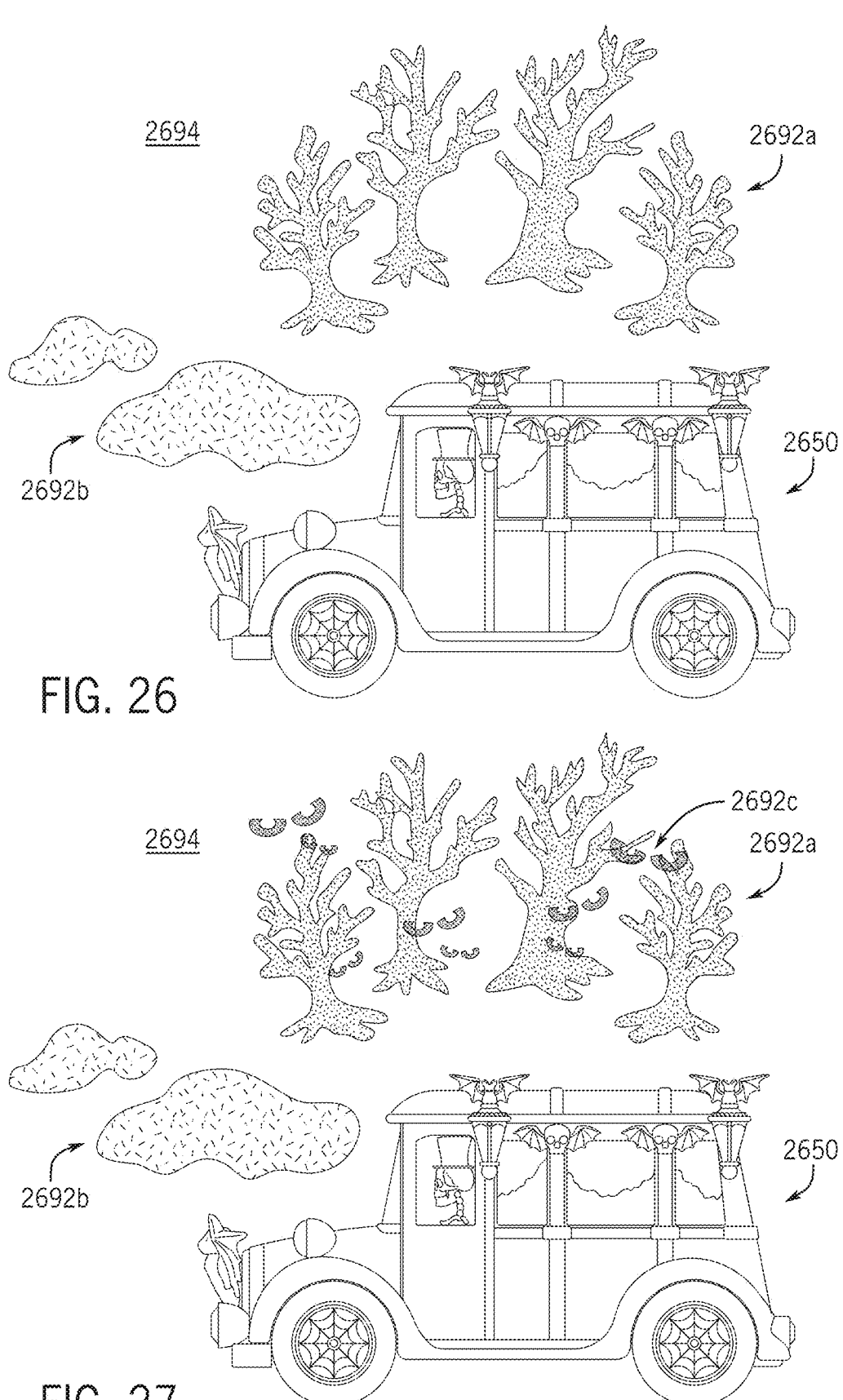
FIG. 26 shows an eighth embodiment of a decorative cover assembly that creates an illuminated effect.
FIG. 27 shows the decorative cover assembly of FIG. 26 at a different period of time.

A decorative cover assembly similar to the decorative cover assembly 2250 of FIGS. 22-25 can be configured to provide timed illuminated projections. For example, the images 2292a and 2292b could remain illuminated any time the fragrance dispenser 2210' is turned on, while the image 2292c could be illuminated for intermittent predetermined time periods. A specific embodiment of such a decorative cover assembly 2650 is shown and described with respect to FIGS. 26 and 27, but it should be understood that the description of the functionality of decorative cover assembly 2650 could apply equally to the decorative cover assembly 2250. Moreover, it should be noted that the decorative cover assembly 2650 has all of the functional components of the decorative cover assembly 2250, and only the aesthetics of the two decorative cover assemblies are different. Therefore, not all of the parts of decorative cover assembly 2650 will be described herein. The main difference is that decorative cover assembly 2650 comprises a controller (e.g., controller 40, FIG. 6) configured to control a first light source and a second light source of the plurality of light sources to turn on and off when the decorative cover assembly 2650 is, as a unit, turned on. The controller is configured to control the first light source to be on and the second light source to be off for a first predetermined period of time. For example, the controller controls first light source(s) to form illuminated images 2692a (e.g., trees) and 2692b (e.g., clouds) on the external surface 2694 for a first predetermined period of time, as shown in FIG. 26. The controller is configured to control the first and second light sources to both be on for a second predetermined period of time subsequent to the first period of time. For example, the controller controls the first light source(s) to form illuminated images 2692a (e.g., trees) and 2692b (e.g., clouds) on the external surface 2694 and controls the second light source to form illuminated images 2692c (e.g., eyes) for the second predetermined period of time, as shown in FIG. 27. The controller is also configured to control the first light source to be on and the second light source to be off for a third predetermined period of time subsequent to the second period of time, in effect returning the projected illuminated images to those shown in FIG. 26 for the third predetermined period of time.

The first, second, and third predetermined periods of time can be any lengths of time. Generally, the second period of time for which the second light source is on (e.g., to add the illuminated image 2692c of eyes) is anywhere between fifteen to thirty minutes, although other time periods could be programmed. The first and third periods of time may be the same or different lengths of time, which may both be longer than the second period of time. The controller may be configured to cycle the second light source off for the first/third time period and on for the second time period for as long as the unit is turned on. In some examples, the controller is configured also to cycle the first light source off, so that no illuminated images are projected onto the external surface 2694 for a given period of time.

Moreover, the controller may be configured to control the second light source to gradually increase in intensity for at least a portion of the second period of time. For example, the illuminated image 2692c of the eyes may be very faint at the beginning of the second period of time and may gradually become brighter as the second period of time continues. The fade-in period may be the same length as the second period of time or may be shorter than the second period of time. In some examples, the fade-in period may be followed by a fade-out period, during which the intensity of the second light source is gradually decreased over time. There may be a period of time within the second period of time in which the second light source remains at full intensity. Alternatively, the second light source made fade-in to full intensity, then immediately fade-out until the second light source is off, thus beginning the third period of time. The controller may control the intensity of the second light source by changing the duty cycle of power provided to the second light source using pulse width modulation.

Figures 28, 29:
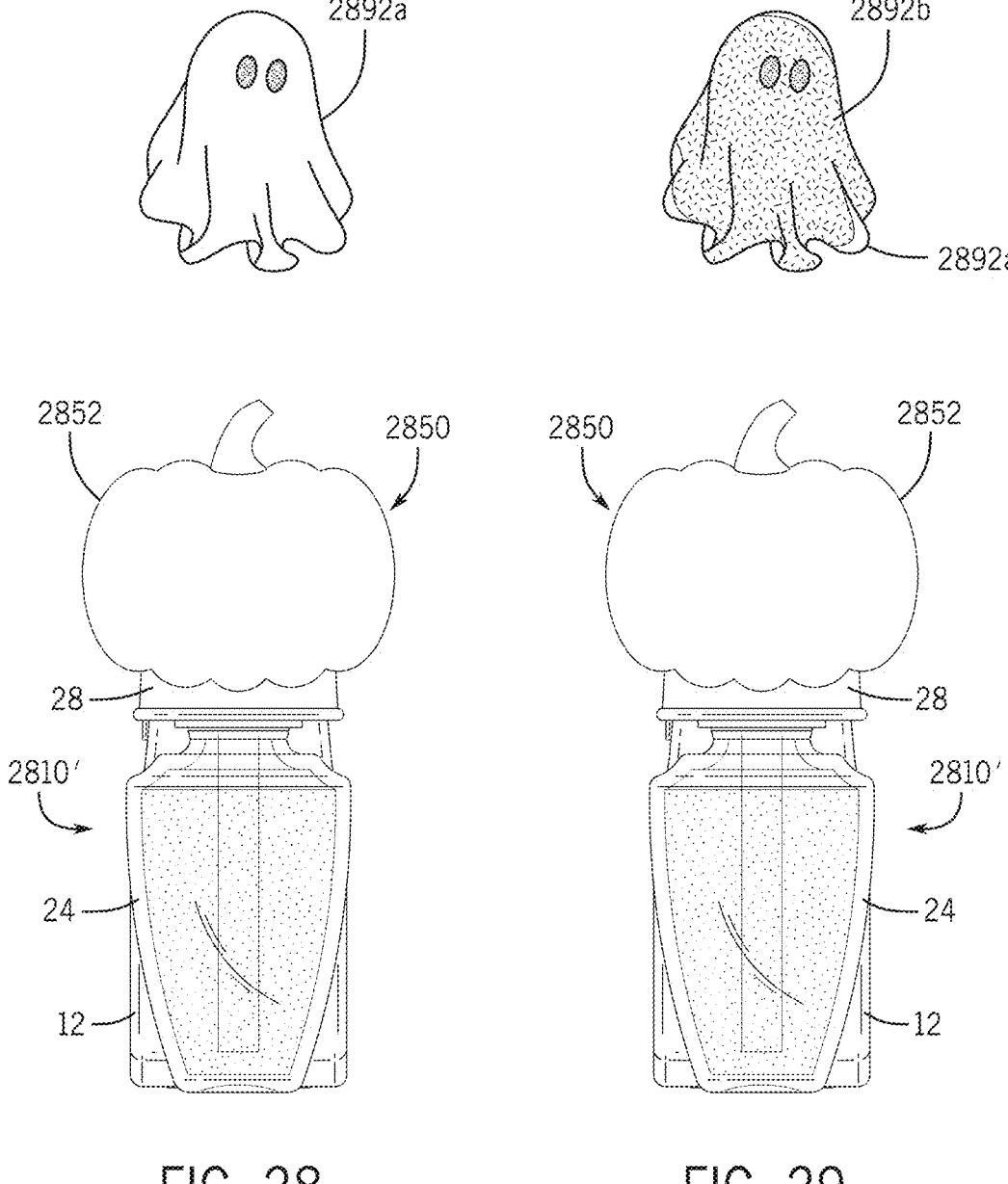
FIG. 28 shows a ninth embodiment of a fragrance dispenser that creates an illuminated effect.
FIG. 29 shows the fragrance dispenser of FIG. 28 at a different period of time.
Figure 30:
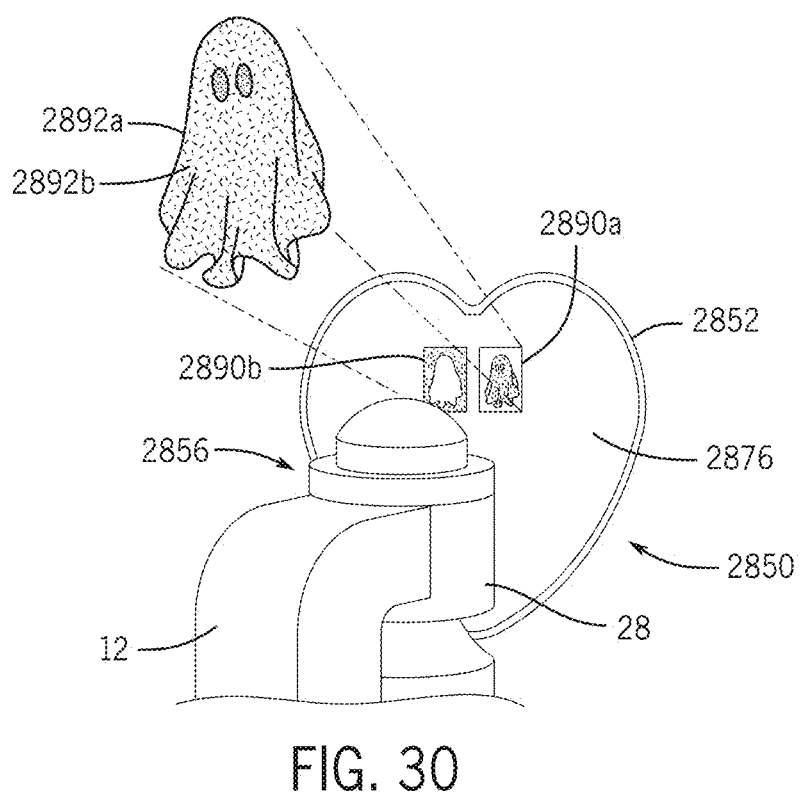
FIG. 30 shows a rear perspective view of the upper portion of the fragrance dispenser of FIGS. 28 and 29.

FIGS. 28-31 show another example of a fragrance dispenser 2810' with a decorative cover assembly 2850 configured to illuminate different light sources at different times. The fragrance dispenser 2810' comprises a housing 12 having a socket portion 28 defining a receptacle configured to receive a bottle 24 having a fragranced liquid therein. The decorative cover assembly 2850 is coupled to the housing 12 and conceals at least part of the socket portion 28. The decorative cover assembly 2850 comprises an outer cover 2852. A backplate 2876 is coupled to the outer cover 2852. The backplate 2876 has a plurality of apertures 2890a, 2890b formed therein. At least one film 2896 has an opaque portion 2898 and at least one translucent portion 2899a, 2899b together defining at least one image. As shown in FIG. 30, a given image of the at least one image is positioned across an aperture 2890a, 2890b in the plurality of apertures in the backplate 2876. The decorative cover assembly 2850 also includes a plurality of light sources 2842a, 2842b, each light source in the plurality of light sources being positioned between the backplate 2876 and the outer cover 2852 and being directed at a respective aperture 2890a, 2890b and the given image positioned thereacross. Light from each respective light source 2842a, 2842b projects through the at least one translucent portion 2899a, 2899b of the at least one film 2896 to form an illuminated version of the given image on an external surface, as shown in FIGS. 28 and 29. In this example, the light source 2842a projects through the translucent portion 2899a to form the image 2892a of the outline and eyes of a ghost (see FIG. 28), and the light source 2842b projects through the translucent portion 2899b to form the image 2892b filling in the body of the ghost (see FIG. 29). A controller (e.g., controller 40, FIG. 6) is configured to control the first light source 2842a and the second light source 2842b of the plurality of light sources to turn on and off. The controller is configured to control the first light source 2842a to be on and the second light source 2842b to be off for a first predetermined period of time, such that only the outline and eyes of the ghost (image 2892a) are shown on the external surface, as shown in FIG. 28. The controller is configured to control the first and second light sources 2842a, 2842b to both be on for a second predetermined period of time subsequent to the first period of time, such that both the outline/eyes of the ghost and the filled-in body of the ghost (images 2892a and 2892b) are shown at the same time, as shown in FIG. 29.

Figure 31:
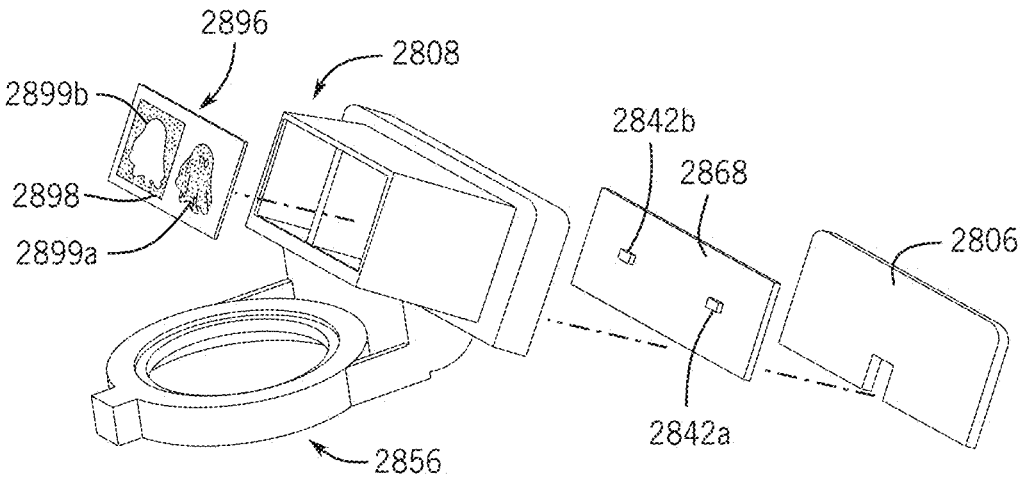
FIG. 31 is an exploded view of several of the components of the decorative cover assembly of the fragrance dispenser of FIGS. 28-30.

As shown in FIG. 31, the decorative cover assembly 2850 further comprises a printed circuit board 2868 on which each of the light sources 2842a, 2842b and the controller (not shown) are held. The PCB 2868 is held by a partitioned housing 2808, such that light from the light source 2842b does not interfere with light from the light source 2842a, and vice versa, within the decorative cover assembly 2850. The partitioned housing 2808 is attached to a collar 2856, which collar 2856 couples the decorative cover assembly 2850 to the housing 12 as shown in FIG. 30 and described with respect to earlier embodiments. A shield plate 2806 is attached to the side of the PCB 2868 that is not adjacent the partitioned housing 2808, which shield plate 2806 prevents light from the light sources 2842a, 2842b from illuminating the inside face of the outer cover 2852. The shield plate 2806 therefore enables the decorative cover assembly 2850 to project an illuminated image on an external surface while also incorporating different illuminated effects on the outer cover 2852, as will be described further herein below. In other examples, the shield plate is omitted. The components shown in FIG. 31, minus the collar 2856, are assembled between the backplate 2876 and the outer cover 2852. The collar 2856 may extend through an aperture formed in the backplate 2876 such that it can be attached to the housing of the fragrance dispenser.

In the example shown here, the plurality of apertures comprises a first aperture 2890a and a second aperture 2890b. The first light source 2842a is directed through one side of the partitioned housing 2808 and at the first aperture 2890a, and the second light source 2842b is directed through another side of the partitioned housing 2808 and at the second aperture 2890b. The at least one translucent portion of the film 2896 includes a first translucent portion 2899a and a second translucent portion 2899b. The first translucent portion 2899a and the opaque portion 2898 of the film 2896 together form a first image of the at least one image positioned across the first aperture 2890a in the backplate 2876, and the second translucent portion 2899b and the opaque portion 2898 together form a second image of the at least one image positioned across the second aperture 2890b in the backplate 2876. In particularly advantageous examples, the first light source 2842a has a different color than the second light source 2842b. For example, the first light source 2842a is orange and the second light source 2842b is green. The partitioned housing 2808 prevents the lights from each light source from interfering with each other so that two distinct images in two distinct colors are projected onto the external surface.

As shown in FIG. 28, when the first light source 2842a is on and the second light source 2842b is off, light from the first light source 2842a projects through the first translucent portion 2899a to form an illuminated version of the first image 2892a on the external surface. As shown in FIG. 29, when the first and second light sources 2842a, 2842b are both on, light from the first light source 2842a projects through the first translucent portion 2899a to form an illuminated version of the first image 2892a on the external surface, and light from the second light source 2842b projects through the second translucent portion 2899b to form an illuminated version of the second image 2892b on the external surface. In particularly advantageous embodiments, the illuminated version of the first image 2892a and the illuminated version of the second image 2892b together form a cohesive image on the external surface. For example, as shown in FIG. 29, the cohesive image is the outline and eyes of a ghost in light of a first color, which outline is filled in with light of a second color. In some examples, the illuminated version of the first image 2892a at least partially overlaps with the illuminated version of the second image 2892b on the external surface. For example, the filled-in ghost shape of the image 2892b overlaps at least the eyes of the first image 2892a. By way of another example, as shown in FIG. 27, the eyes of image 2692c overlap with the trees of image 2692a. In other examples, there is no overlap of the illuminated images. In examples in which there is overlap and/or alignment of illuminated images, the relative locations of the light sources, apertures in the backplate, and images on the film are configured to provide the desired effect on the external surface, which is situated at a known distance from the light sources given that the dimensions of the housing 12 are known.

As with the description of FIGS. 26 and 27, the controller of the decorative cover assembly 2850 may control the first and second light sources 2842a, 2842b to be on or off for given overlapping or non-overlapping periods of time and/or to fade in or fade out over given periods of time to create a desired illuminated effect.

Outer Covers with Invisible Ink

Figure 33:
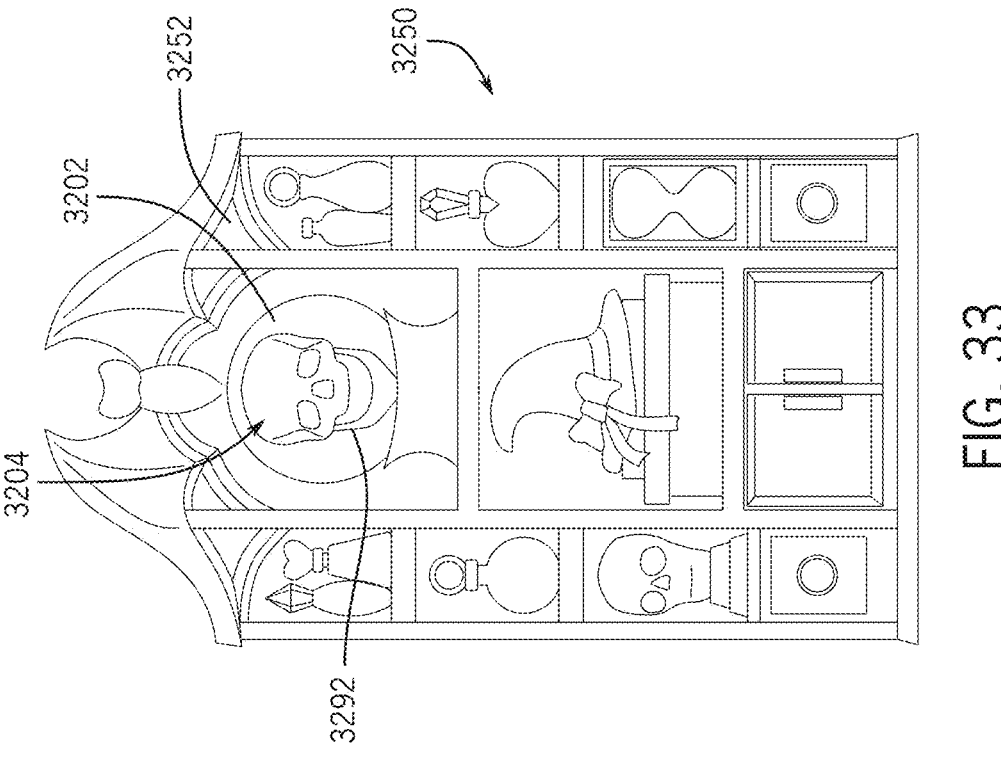
FIG. 33 shows the decorative cover assembly of FIG. 32 at a different period of time.
Figure 32:
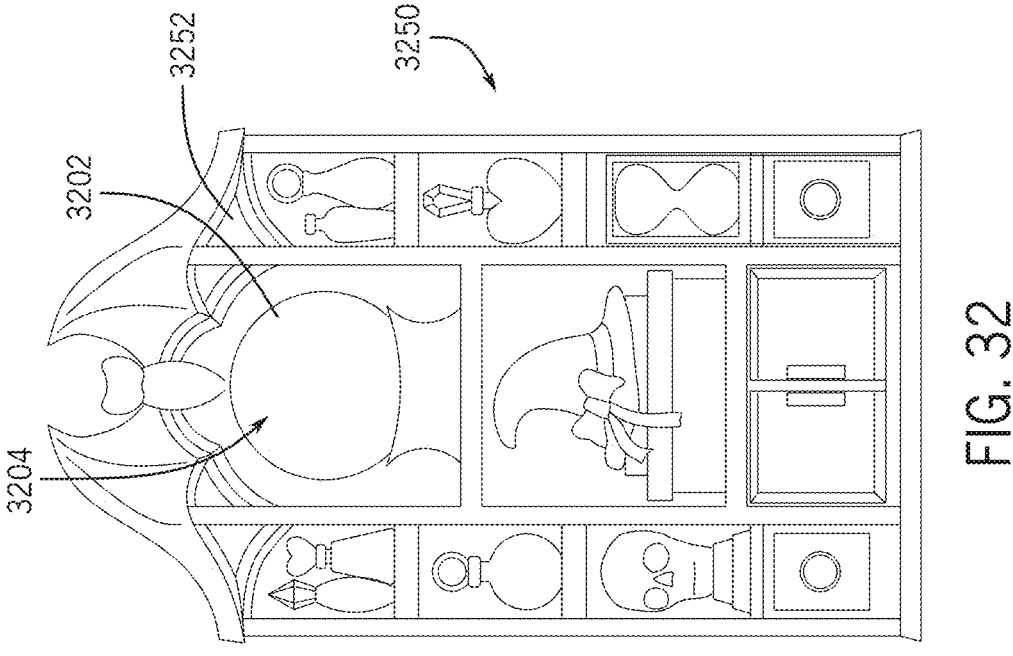
FIG. 32 shows a tenth embodiment of a decorative cover assembly that creates an illuminated effect.
Figure 34:
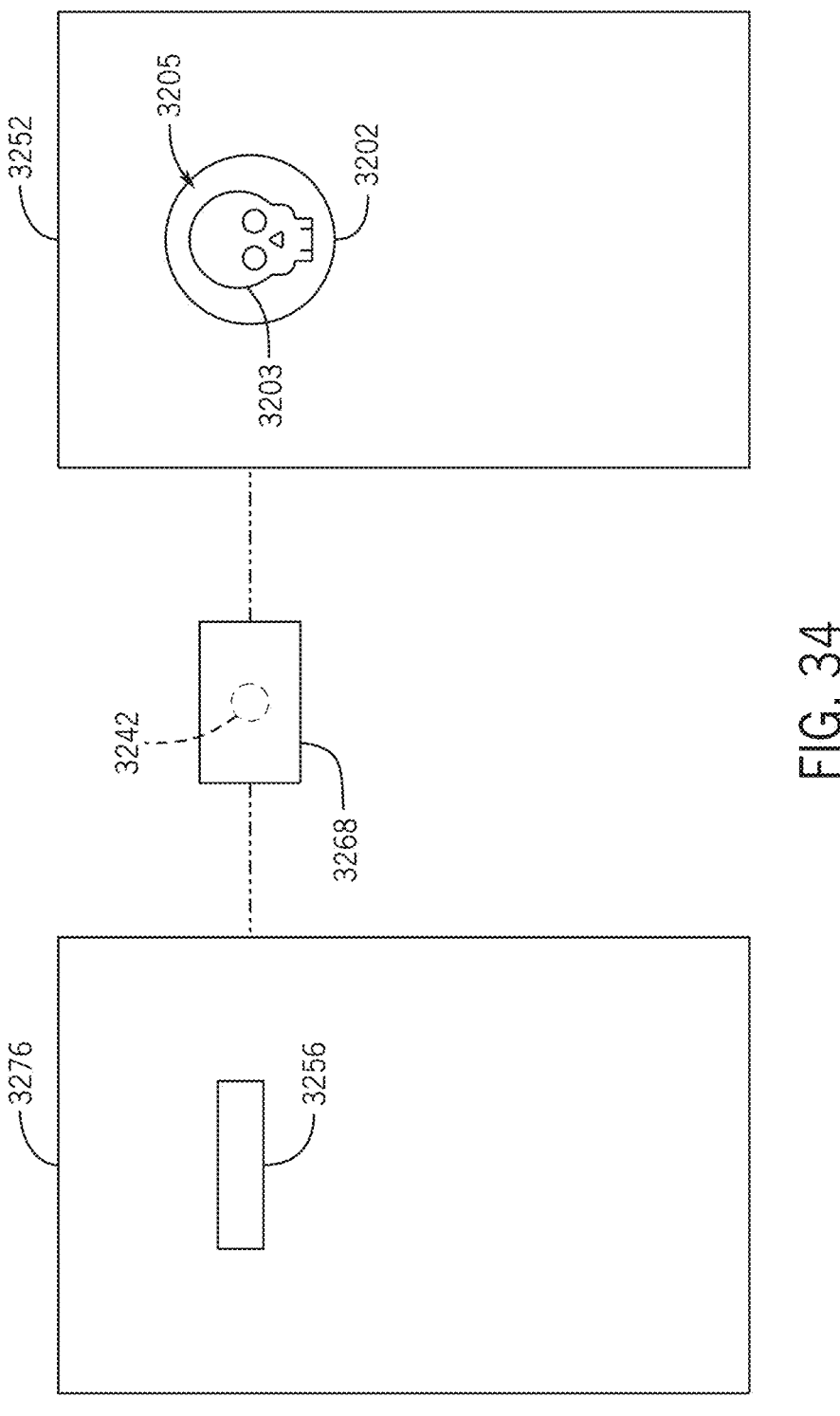
FIG. 34 is a schematic exploded view showing parts of the decorative cover assembly of FIGS. 32 and 33.

FIGS. 32 and 33 show another embodiment of a decorative cover assembly 3250 for a fragrance dispenser. The fragrance dispenser is in this example hidden by the decorative cover assembly 3250, but comprises a housing having a socket portion defining a receptacle configured to receive a bottle having a fragranced liquid therein, as described hereinabove with respect to FIGS. 1-5. The decorative cover assembly 3250 is coupled to the housing and conceals at least part (here, all) of the socket portion. The decorative cover assembly 3250 comprises an outer cover 3252 comprising a translucent part 3202 having an inner surface (shown schematically at 3205, FIG. 34) facing the housing of the fragrance dispenser and an outer surface 3204 (FIGS. 32, 33) opposite the inner surface 3205. Here, the translucent part 3202 is a "crystal ball" made of a circular plate, which may be flat or convex. As shown schematically in FIG. 34, at least one light source 3242 is positioned between the housing and the outer cover 3252. The light source 3242 is on the opposite side of the PCB 3268 shown here and so is shown in phantom. A backplate 3276 supports the PCB 3268 and is attached on its rear side to a collar 3256 like that shown in the embodiments described hereinabove, which in turn is supported on the housing of the fragrance dispenser.

As shown in FIG. 33, at least one illuminated image 3292 is visible on the outer surface 3204 of the translucent part 3202 of the outer cover 3252 when the at least one light source is on. As shown in FIG. 32, the at least one illuminated image is not visible on the outer surface 3204 of the translucent part 3202 of the outer cover 3252 when the light source is off. The at least one illuminated image 3292 is formed with ultraviolet-visible ink 3203 applied to the inner surface 3205 of the translucent part 3202 of the outer cover 3252. The at least one light source 3242 is an ultraviolet light source such that when the at least one light source 3242 is illuminated, the ultraviolet-visible ink 3203 is visible. In another example, the UV-visible ink 3203 is printed on the outer surface 3204 of the translucent part 3202 of the outer cover 3252; however, there may be advantages to printing the UV-visible ink 3203 on the inner surface 3205 in that the outer surface 3204 appears completely uniform from the outside of the decorative cover assembly 3250. Further, the illuminated image 3292 may appear to "float" behind the outer surface 3204 if the UV-visible ink 3203 is printed on the inner surface 3205.

Figures 35, 36:
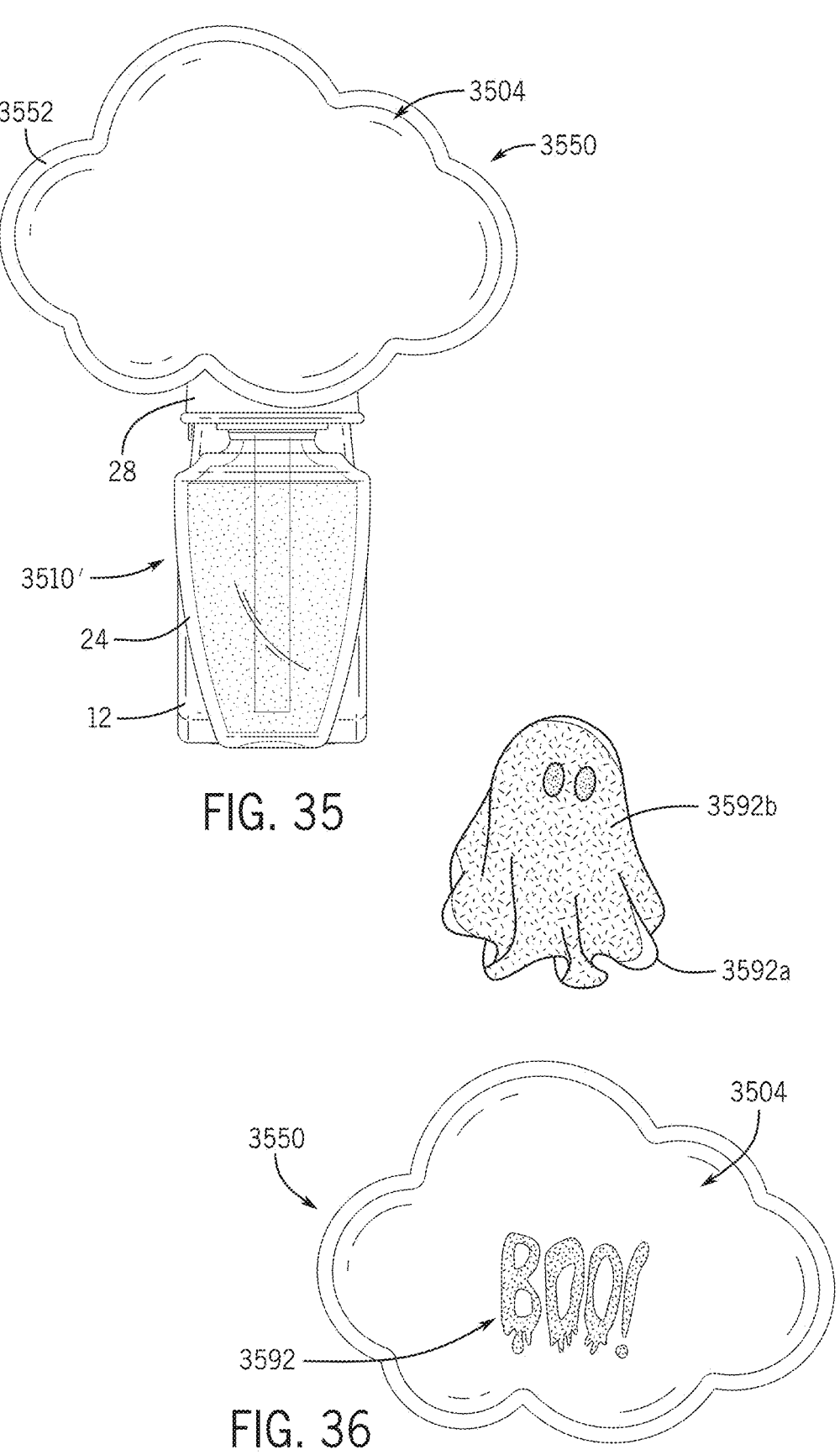
FIG. 35 shows an eleventh embodiment of a fragrance dispenser with a decorative cover assembly that creates an illuminated effect.
FIG. 36 shows the decorative cover assembly of FIG. 35 at a different period of time.
Figure 37:
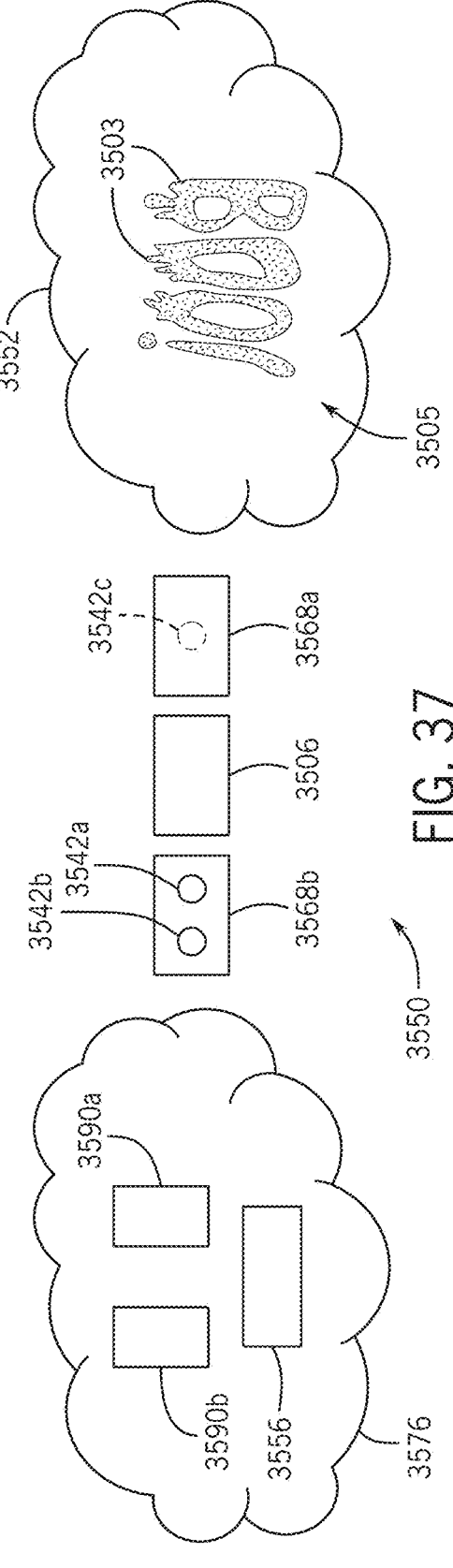
FIG. 37 is a schematic exploded view showing parts of the decorative cover assembly of FIGS. 35 and 36.

FIGS. 35-37 show another example of a decorative cover assembly 3550 for a fragrance dispenser 3510', which is constructed similarly to the fragrance dispenser described with respect to FIGS. 1-5. In this example, the entire outer cover 3552 is the translucent part. By comparing FIG. 35 with FIG. 36, it can be seen that at least one illuminated image 3592 (the word "BOO") is visible on the outer surface 3504 of the translucent outer cover 3552 when the UV light source 3542c is on, and the at least one illuminated image is not visible on the outer surface 3504 of the translucent outer cover 3552 when the UV light source 3542c is off. The illuminated image 3592 is formed with ultraviolet-visible ink 3503 (FIG. 37) applied to the inner surface 3505 of the translucent outer cover 3552. FIGS. 36 and 37 also show how the concept of the embodiment of FIGS. 28-31 can be combined with the concept of the embodiment of FIGS. 32-34 in one decorative cover assembly 3550. That is, the decorative cover assembly 3550 is provided with a film (not shown) having an opaque portion and a translucent portion together defining an image, which image is positioned across an aperture 3590a, 3590b in a backplate 3576 of the cover assembly 3550, and a non-UV light source 3542a, 3542b is arranged to project through the translucent portion of the film to form an illuminated version of the image 3592a, 3592b on an external surface. The components and operation of such an assembly are described above with respect to FIGS. 28-31 and will not be described in detail here.

The present inventors discovered that if an entirely translucent outer cover 3552 is used, light from the light sources 3542a, 3542b that are intended for creating the projected images 3592a, 3592b on the external surface will wash out the illuminated image 3592 formed by the UV-visible ink. Therefore, in embodiments in which the light sources include both an ultraviolet light source 3542c and a non-ultraviolet light source 3542a, 3542b, a shield plate 3506 is also provided. The shield plate 3506 is positioned between the ultraviolet light source 3542c on PCB 3568a, which projects forwardly toward the outer cover 3552, and the non-ultraviolet light sources 3542a, 3542b on PCB 3568b, which project rearwardly. The shield plate 3506 prevents light from the non-ultraviolet light sources 3542a, 3542b from projecting onto the inner surface 3505 of the outer cover 3552, such that the only light from the decorative cover assembly 3550 that projects directly onto the outer cover 3552 is the UV light source 3542c. The shield plate 3506 may have any size and shape required to accomplish its purpose. One non-schematic example of such a shield plate is shown at 2806 in FIG. 31, which shield plate 2806 may be combined with a partitioned housing 2808 to further prevent light from the non-UV light sources from illuminating the outer cover 3552.

The translucent parts of the outer covers (e.g., the translucent part 3202 of outer cover 3252 of FIG. 32 or the entire outer cover 3552 of FIG. 35) may be made of a plastic such as polycarbonate or polypropylene that is tinted to render the part translucent. In particularly preferred embodiments, the tinting is enough to hide the functional components behind the translucent part from view when the unit is not illuminated. However, the tinting is light enough that the UV-visible ink is easily visible through the material of the outer cover 3252, 3552 when the UV light source is on. The UV-visible ink 3203, 3503 (also referred to as "invisible ink") can be pad printed or masked and sprayed onto the translucent part 3202, 3552. A UV-protective topcoat can be applied over the UV-visible ink 3203, 3503 in order to prevent the UV-visible ink 3203, 3503 from fading. The UV light sources 3242, 3542c are LEDs that emit long-wave (UV-A) ultraviolet light and are also known as "blacklights."

Outer Cover with Projected Images

Figure 38:
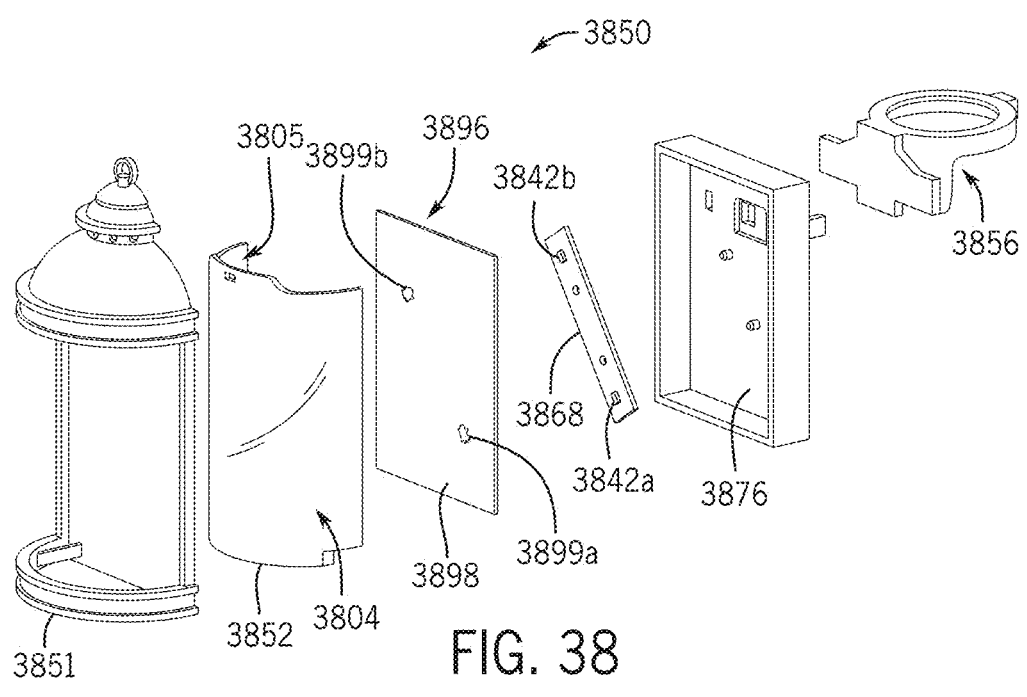
FIG. 38 is an exploded view of parts of a twelfth embodiment of a decorative cover assembly.
Figure 39:
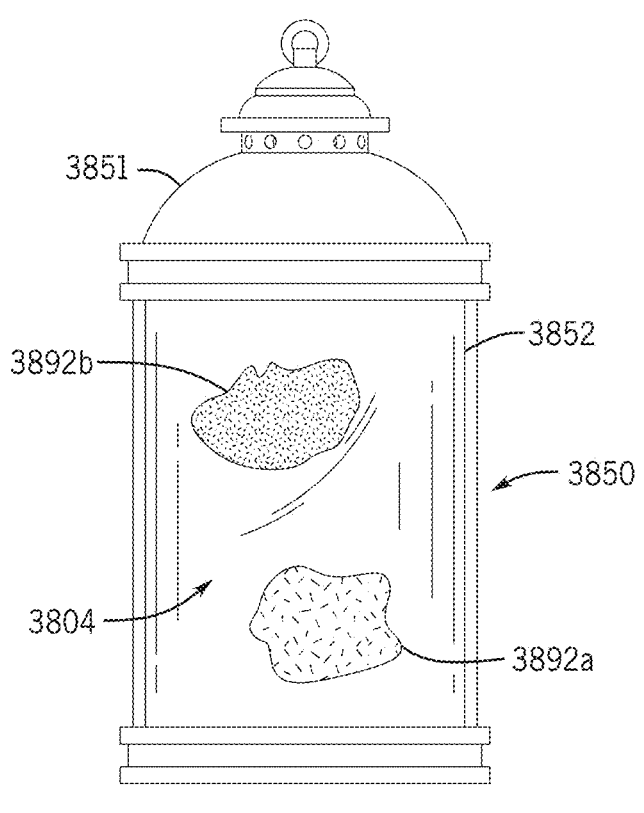
FIG. 39 shows the decorative cover assembly of FIG. 38 in an assembled, illuminated state.

FIGS. 38 and 39 illustrate another embodiment of a decorative cover assembly 3850 for a fragrance dispenser, which is constructed similarly to the fragrance dispenser described with respect to FIGS. 1-5. The decorative cover assembly 3850 comprises a trim piece 3851 and an outer cover 3852 comprising a translucent part (here, the entire outer cover 3852) having an inner surface 3805 facing the housing of the fragrance dispenser and an outer surface 3804 opposite the inner surface 3805. At least one light source 3842a, 3842b is positioned on a PCB 3868 between the outer cover 3852 and the housing (which is coupled to the backplate 3876 via the collar 3856). A film 3896 is positioned between the light source 3842a, 3842b and the outer cover 3852. The film 3896 has an opaque portion 3898 and at least one translucent portion 3899a, 3899b together defining an image. Light from the at least one light source 3842a, 3842b projects through the at least one translucent portion 3899a, 3899b of the film 3896 to form at least one illuminated image 3892a, 3892b on the inner surface 3805 of the translucent part of the outer cover 3852, which is visible on the outer surface 3804 of the translucent part of the outer cover 3852, seeing as the outer cover 3852 is translucent. The at least one illuminated image 3892a, 3892b is visible on the outer surface 3804 of the translucent part of the outer cover 3852 when the at least one light source 3842a, 3842b is on, as shown in FIG. 39. The at least one illuminated image 3892a, 3892b is not visible on the outer surface 3804 of the translucent part of the outer cover 3852 when the light source 3842a, 3842b is off.

As shown, the at least one translucent portion of the film 3896 comprises a first translucent portion 3899a and a second translucent portion 3899b. The at least one light source comprises a first light source 3842a aligned with the first translucent portion 3899a and a second light source 3842b aligned with the second translucent portion 3899b. Light from the first light source 3842a projects through the first translucent portion 3899a of the film 3896 to form a first illuminated image 3892a of the at least one illuminated image on the inner surface 3805 of the translucent part of the outer cover 3852, which is visible on the outer surface 3804 of the translucent part of the outer cover 3852. Light from the second light source 3842b projects through the second translucent portion 3899b of the film 3896 to form a second illuminated image 3892b of the at least one illuminated image on the inner surface 3805 of the translucent part of the outer cover 3852, which is visible on the outer surface 3804 of the translucent part of the outer cover 3852.

The outer cover 3852 can be curved as shown here or could have another shape, such as a prism or a flat plate. The outer cover 3852 could be frosted, glossy, or flat and can be made of plastic or glass. The outer cover 3852 could be tinted white or with a color. The film 3896 can be an acrylic sheet that is pad printed with black ink, leaving the translucent portions 3899a, 3899b clear. Alternatively, the film 3896 can be vacuum plated with an opaque deposit, after which the translucent portions 3899a, 3899b are etched into the deposited layer.

A controller (e.g., controller 40, FIG. 6) is configured to control the first and second light sources 3842a, 3842b to turn on and off. The controller is configured to do at least one of the following: simultaneously turn the first light source 3842a on and the second light source 3842b off; simultaneously turn the first and second light sources 3842a, 3842b on (see FIG. 39); and simultaneously turn the first and second light sources 3842a, 3842b off. In some examples, the controller is configured to control the first light source 3842a to be on and the second light source 3842b to be off for a first predetermined period of time, and the controller is configured to control the first and second light sources 3842a, 3842b to both be on for a second predetermined period of time subsequent to the first period of time. The controller is configured to cycle through the first and second periods of time for as long as the unit is turned on, or for a predetermined time period. The controller may also be configured to fade-in one or both of the light sources from off to full intensity, and to fade-out one or both of the light sources from full intensity to off. In some examples, the first light source 3842a has a different color than the second light source 3842b, although both light sources could have the same color.

In some examples, the concept of FIGS. 38 and 39 is combined with the projection concepts described hereinabove.

In the present description, certain terms have been used for brevity, clarity, and understanding. No unnecessary limitations are to be implied therefrom beyond the requirement of the prior art because such terms are used for descriptive purposes only and are intended to be broadly construed. The different assemblies described herein may be used alone or in combination with other systems. Various equivalents, alternatives, and modifications are possible within the scope of the appended claims.

What is claimed is:

1. A fragrance dispenser comprising:
   a housing having a socket portion defining a receptacle configured to receive a bottle having a fragranced liquid therein;
   a decorative cover assembly coupled to the housing and concealing at least part of the socket portion, wherein the decorative cover assembly comprises:
   an outer cover;
   a backplate coupled to the outer cover, the backplate having a plurality of apertures formed therein;
   at least one film having an opaque portion and at least one translucent portion together defining at least one image, a given image of the at least one image being positioned across an aperture in the plurality of apertures; and
   a plurality of light sources, each light source in the plurality of light sources being positioned between the backplate and the outer cover and being directed at a respective aperture and the given image positioned thereacross;
   wherein light from each respective light source projects through the at least one translucent portion of the at least one film to form an illuminated version of the given image on an external surface; and
   a controller configured to control a first light source and a second light source of the plurality of light sources to turn on and off;
   wherein the controller is configured to control the first light source to be on and the second light source to be off for a first predetermined period of time;
   wherein the controller is configured to control the first and second light sources to both be on for a second predetermined period of time subsequent to the first period of time;
   wherein the plurality of apertures comprises a first aperture and a second aperture, the first light source being directed at the first aperture and the second light source being directed at the second aperture;
   wherein the at least one translucent portion includes a first translucent portion and a second translucent portion, wherein the first translucent portion and the opaque portion together form a first image of the at least one image positioned across the first aperture and the second translucent portion and the opaque portion together form a second image of the at least one image positioned across the second aperture;

wherein when the first light source is on and the second light source is off, light from the first light source projects through the first translucent portion to form an illuminated version of the first image on the external surface; and wherein when the first and second light sources are both on, light from the first light source projects through the first translucent portion to form an illuminated version of the first image on the external surface and light from the second light source projects through the second translucent portion to form an illuminated version of the second image on the external surface.

2. The fragrance dispenser of claim 1, wherein the illuminated version of the first image and the illuminated version of the second image together form a cohesive image on the external surface.

3. The fragrance dispenser of claim 1, wherein the illuminated version of the first image at least partially overlaps with the illuminated version of the second image on the external surface.

4. The fragrance dispenser of claim 1, wherein the controller is configured to control the second light source to gradually increase in intensity for at least a portion of the second period of time.

5. The fragrance dispenser of claim 1, wherein the controller is configured to control the first light source to be on and the second light source to be off for a third predetermined period of time subsequent to the second period of time.

6. The fragrance dispenser of claim 1, wherein the decorative cover assembly further comprises a printed circuit board on which each of the light sources and the controller are held.

7. The fragrance dispenser of claim 1, further comprising a collar coupling the decorative cover assembly to the housing.

8. The fragrance dispenser of claim 1, wherein the first light source has a different color than the second light source.

9. The fragrance dispenser of claim 1, wherein the illuminated version of the given image forms a scene together with the decorative cover assembly.

10. A fragrance dispenser comprising:

a housing having a socket portion defining a receptacle configured to receive a bottle having a fragranced liquid therein; and a decorative cover assembly coupled to the housing and concealing at least part of the socket portion, wherein the decorative cover assembly comprises:

an outer cover comprising a translucent part having an inner surface facing the housing and an outer surface opposite the inner surface;

at least one light source positioned between the housing and the outer cover; and a film positioned between the at least one light source and the outer cover, the film having an opaque portion and at least one translucent portion together defining an image;

wherein at least one illuminated image is visible on the outer surface of the translucent part of the outer cover when the at least one light source is on;

wherein the at least one illuminated image is not visible on the outer surface of the translucent part of the outer cover when the light source is off;

wherein light from the at least one light source projects through the at least one translucent portion of the film to form the at least one illuminated image on the inner surface of the translucent part of the outer cover, which is visible on the outer surface of the translucent part of the outer cover;

wherein the at least one translucent portion of the film comprises a first translucent portion and a second translucent portion;

wherein the at least one light source comprises a first light source aligned with the first translucent portion and a second light source aligned with the second translucent portion;

wherein light from the first light source projects through the first translucent portion of the film to form a first illuminated image of the at least one illuminated image on the inner surface of the translucent part of the outer cover, which is visible on the outer surface of the translucent part of the outer cover;

wherein light from the second light source projects through the second translucent portion of the film to form a second illuminated image of the at least one illuminated image on the inner surface of the translucent part of the outer cover, which is visible on the outer surface of the translucent part of the outer cover; and wherein the fragrance dispenser further comprises a controller configured to control the first and second light sources to turn on and off, wherein the controller is further configured to do at least one of the following:

simultaneously turn the first light source on and the second light source off:

simultaneously turn the first and second light sources on; and simultaneously turn the first and second light sources off.

11. The fragrance dispenser of claim 10, wherein the first light source has a different color than the second light source.

12. The fragrance dispenser of claim 10, further comprising a collar coupling the decorative cover assembly to the housing.

* * * * *